(12) United States Patent
Liu et al.

(10) Patent No.: US 8,264,174 B2
(45) Date of Patent: Sep. 11, 2012

(54) LASER ACCELERATION SYSTEM FOR GENERATING MONOENERGETIC PROTONS

(75) Inventors: Chuan Sheng Liu, Silver Spring, MD (US); Xi Shao, Potomac, MD (US); Vipin Tripathi, New Delhi (IN); Jao-Jang Su, Potomac, MD (US); Tung-Chang Liu, College Park, MD (US)

(73) Assignee: University of Maryland, College Park, MD (US)

( * ) Notice: Subject to any disclaimer, the term of this patent is extended or adjusted under 35 U.S.C. 154(b) by 226 days.

(21) Appl. No.: 12/843,520

(22) Filed: Jul. 26, 2010

(65) Prior Publication Data
US 2011/0273115 A1    Nov. 10, 2011

Related U.S. Application Data

(60) Provisional application No. 61/228,360, filed on Jul. 24, 2009.

(51) Int. Cl.
*H05H 15/00* (2006.01)
*H01J 3/14* (2006.01)

(52) U.S. Cl. .................................... 315/500; 250/396 R
(58) Field of Classification Search .......... 315/500–507; 600/1; 250/396 R
See application file for complete search history.

(56) References Cited

U.S. PATENT DOCUMENTS

| | | | |
|---|---|---|---|
| 2004/0018700 A1* | 1/2004 | Cowan et al. | 438/513 |
| 2006/0145088 A1* | 7/2006 | Ma | 250/396 ML |
| 2009/0230318 A1* | 9/2009 | Fourkal et al. | 250/423 R |
| 2011/0313232 A1* | 12/2011 | Balakin | 600/1 |

* cited by examiner

*Primary Examiner* — Don Le
(74) *Attorney, Agent, or Firm* — Carter, DeLuca, Farrell & Schmidt, LLP

(57) ABSTRACT

A proton acceleration system is provided for accelerating protons within a target. The system includes a laser source generating a laser beam having a wavelength $\lambda_L$ and intensity and a target formed of foil having a selected thickness. The target is irradiated by the laser beam and transformed into a plasma that has a target density. This causes a treatment energy to be emitted from the foil due to the irradiation. The thickness of the foil of the target is selected so that the foil has a thickness within a range of optimal thickness $\Delta_s$ to $2\times\Delta_s$, wherein $\Delta_s$ is less than the laser wavelength and is a function of the laser intensity, laser wavelength, and target density sufficient to achieve radiation pressure acceleration (RPA).

34 Claims, 19 Drawing Sheets

LASER ACCELERATION SYSTEM FOR GENERATING MONOENERGETIC PROTONS

PRIORITY

This application claims priority to Provisional U.S. Application No. 61/228,360 filed Jul. 24, 2009.

BACKGROUND

The present disclosure relates generally to an acceleration system for generating monoenergetic protons. The present disclosure relates more particularly to an acceleration system for generating monoenergetic protons that has a sufficient acceleration gradient to achieve a compact system. Oncology or cancer treatment using energetic protons is a well-established approach to treatment due to the favorable ballistic and range properties of proton beams. The advantage of proton therapy lies in a pronounced peak, known in the art as Bragg's peak, of energy loss of ionizing radiation along the path of the accelerated protons. Physicians can precisely deliver the radiation dose to the target and greatly reduce the damage to normal cells and tissues. However, major problems of the current sources of energetic protons used in cancer therapy are cost and the large size of the installation. At present, conventional proton therapy centers can cost from $100M to $200M due to the size and complexity of the existing proton generating technology. Currently available cyclotron accelerator-based proton therapy systems are large and cost ~$150 million. Currently available synchrotron based proton accelerators are expensive (costing >$100 million each) and occupy a larger space than can fit into a standard room in a building, making it nearly impossible to install in a community hospital and generalize its usage.

Another disadvantage to currently available proton therapy systems is that the minimum size of the beam spot of the delivered energy is limited to millimeter, which lacks precision for intricate treatments.

One possible source of laser proton therapy, Target Normal Sheath Acceleration (TNSA) with laser radiation on thick targets of thickness>laser wavelength to produce energetic protons, has proven unsuitable for medical applications because the energy spectrum is broad, few protons reach the maximum energy, the efficiency of energy conversion to energetic protons is low. A >1 Peta-Watt laser source is required to achieve 60 MeV protons, even with a low quality proton beam having large energy spread.

SUMMARY

The present disclosure is directed to a proton acceleration system for accelerating protons within a target. The system includes a laser source generating a laser beam having a wavelength $\lambda_L$ and intensity and a target formed of foil having a selected thickness. The target is irradiated by the laser beam and transformed into plasma that has a target density. This causes a treatment energy to be emitted from the foil due to the irradiation. The thickness of the foil of the target is selected so that the foil has a thickness within a range of optimal thickness $\Delta_s$ to $2\times\Delta_s$, wherein $\Delta_s$ is less than the laser wavelength and is a function of the laser intensity, laser wavelength, and target density sufficient to achieve radiation pressure acceleration (RPA).

The present disclosure is also directed to a controller for a proton acceleration system including a laser source generating a pulsed laser beam having a wavelength $\lambda_L$ and intensity. The system also includes a target formed of foil which is irradiated by the laser beam and transformed into plasma having a target density causing a treatment energy to be emitted from the foil due to the irradiation. The controller includes a tangible processor and a memory with instructions to be executed by the tangible processor for selecting a thickness of the foil of the target so that the foil has a thickness within a range of optimal thickness $\Delta_s$ to $2\times\Delta_s$, wherein $\Delta_s$ is less than the laser wavelength and is a function of the laser intensity, laser wavelength, and target density sufficient to achieve radiation pressure acceleration (RPA).

The present disclosure is also directed to a method for controlling a proton acceleration system. The system includes a laser source generating a pulsed laser beam having a wavelength $\lambda_L$ and intensity, and further including a target formed of foil which is irradiated by the laser beam and transformed into plasma having a target density causing a treatment energy to be emitted from the foil due to the irradiation.

The method includes selecting a thickness of the foil of the target so that the foil has a thickness within a range of optimal thickness $\Delta_s$ to $2\times\Delta_s$, wherein $\Delta_s$ is less than the laser wavelength and is a function of the laser intensity, laser wavelength, and target density sufficient to achieve radiation pressure acceleration (RPA).

Other features of the presently disclosed network printing system will become apparent from the following detailed description, taken in conjunction with the accompanying drawings, which illustrate, by way of example, the presently disclosed network printing system.

BRIEF DESCRIPTION OF THE DRAWINGS

Various embodiments of the present disclosure will be described below with reference to the figures, wherein.

DETAILED DESCRIPTION

Figure 1:
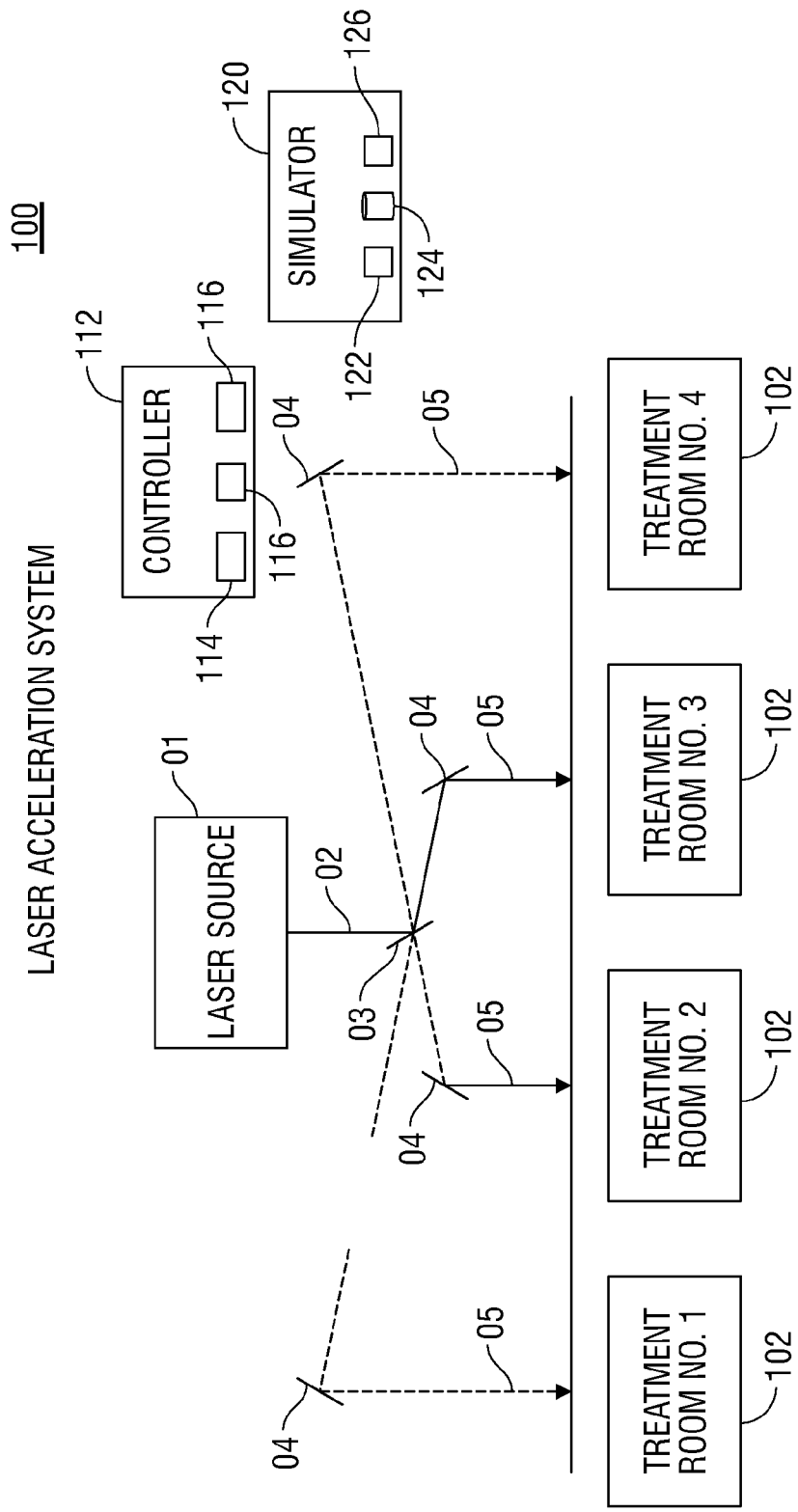
FIG. 1 is a schematic illustration of an exemplary layout of a laser acceleration system in accordance with the present disclosure.

Referring now to the drawing figures, in which like reference numerals identify identical or corresponding elements, the laser acceleration system and method in accordance with the present disclosure will now be described in detail. With initial reference to FIG. 1, an exemplary laser delivery system with laser proton acceleration in accordance with the present disclosure is illustrated and is designated generally as laser delivery system 100.

The laser delivery system 100 generates monoenergetic protons by illuminating an over-dense plasma target formed from an ultra-thin foil (thickness<$\lambda$) with a short pulse, intense laser. The high-intensity of laser is in the order of approximately >$10^{20}$ W/cm$^2$ or >100 TeraWatt. The applied laser light is circularly polarized and is applied with pre-pulses having a high contrast ratio. The foil has an optimally selected thickness so that a self-organized double layer of trapped protons and electrons is formed in the foil. Radiation Pressure Acceleration (RPA) collectively accelerates the double layer as a whole, forming a "light sail." An acceleration gradient is achieved that provides for generating proton energy in the order of multi-GeV even while the size of the laser acceleration system is compact, such suitable for a table-top design.

An appropriate target design is selected to suppress Rayleigh-Taylor (R-T) instabilities. An appropriate laser beam profile design is selected to confine the targeted particles. A magnetic field may be applied to prevent off-axis movement along the z-axis, which is defined by the laser propagation direction, of the electrons which would cause unwanted target transparency. Simulations, described below, have been performed that confirm the expected results. The delivery system 100 has application to proton therapy for treating cancer as well as other applications, including laser induced fusion and fast ignition in laser fusion.

The flexible geometry of the laser delivery system 100 can make proton therapy for cancer patients readily accessible relatively low-cost. Simulations and numerical analyses have demonstrated that the proton energy generated by the laser delivery system 100 is of sufficient quantity and intensity for proton-based cancer therapy.

Aspects of the disclosure are described in the following references which are all incorporated by reference herein:

List Of References

1. Liu et al., "Laser Acceleration of Mono-energetic Protons", Univ. of MD, Energy and Envir. Medicine and Biology, East West Space Sci. Ctr.
2. Liu et al., "Laser Acceleration of Monoenergetic Protons Trapped in Moving Double Layer", East West Space Science Cntr., Univ. of MD.
3. Liu et al., "Laser Hadron Accelerator for Medical Uses", Univ. of MD Ntnl. Cancer Inst., East-West Space Science Cntr., Univ. of MD.
4. Proposal, "Development of Laser Particle Accelerator for Cancer Treatment and Other Medical Applications", Univ. of MD and Lawrence Livermore Ntnl. Lab.
5. Eliasson et al., "Laser acceleration of monoenergetic protons via a double layer emerging from an ultra-thin foil", New Journal of Physics, 11 (2009) 073006 (19 pp).
6. Presentation, "Criteria for Efficient Monoenergetic Ion Acceleration in Radiation Pressure Acceleration (RPA)".
7. Tripathi et al., "Laser acceleration of monoenergetic protons in a self-organized double layer from thin foil", Plasma Pys. & Controlled Fusion, 51 (2009) 024014 (9 pp)
8. Proposal, "Laser Acceleration of Quasi-monoenergetic Protons via Radiation Pressure Driven Thin Foil".
9. Sassi et al., "Sulfur Recovery from Acid Gas Using the Claus Process and High Temp. Air Combustion (HiTAC) Technology", Amer. Journ. of Env. Sci. 4 (5):502-511 (2008).

1. Overview of the Laser Acceleration System

Figure 2:
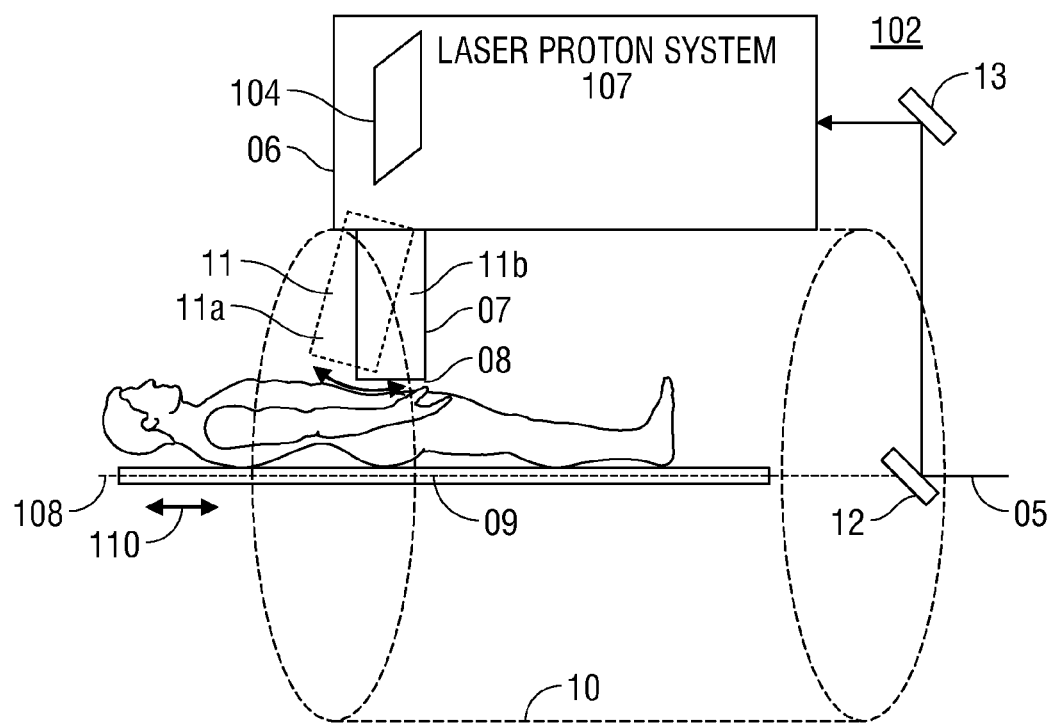
FIG. 2 is a schematic perspective side view of a treatment room layout of the laser acceleration system shown in FIG. 1 in accordance with the present disclosure.
Figure 3:
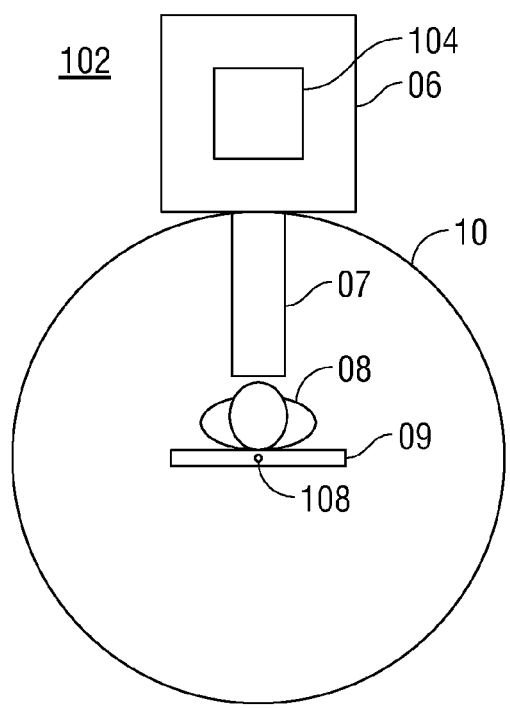
FIG. 3 is a schematic front view of the treatment room layout shown in FIG. 2.

The exemplary laser delivery system 100 shown in FIGS. 1-3 includes a laser source 01 generating a main laser beam 02. The laser energy is tunable by changing the pumping power of the laser. The laser pulse duration is in the order of tens of a femtosecond, and the repeating rate for the laser pulse for medical uses is in the order of 1-10 Hz. When the objective is to produce monoenergetic proton energy, the laser beam 02 may have particular parameters and characteristics for achieving the generation of monoenergetic energy. For example, to achieve monoenergetic energy generation the laser beam is circularly polarized and high intensity with laser power ranging from 100 TeraWatts to 1 PetaWatt. The laser beam may include a main pulse and pre-pulses, as described further below. The output monoenergetic energetic proton energy can be tuned by tuning the incident laser power.

The laser delivery system 100 further includes a steering system that is applicable to laser treatment of any type of energy, including monenergetic, quasi-energetic, etc., energy. The steering system includes a steering mirror 03 that is struck by the laser beam directly from the laser source 01. The steering mirror 03 can be pivoted or rotated for directing the laser beam 02 to a target treating area selected from a plurality of target treating areas. Here the plurality of target treating areas are shown as treatment rooms 102 numbered 1-4. The treatment rooms 102 may be rooms defined by structural dividers such as walls or curtains. Alternatively, there may be no structural features for differentiating between the treatment rooms 102.

The laser delivery system 100 further includes a controller 112 including at least one processor 114 and a computer readable medium 116. The processor 114 executes a control module 118 described further below. The control module 118 including a series of programmable instructions capable of being executed by the processor 114. The series of programmable instructions can be stored on computer-readable medium 116 accessible by the processor 114, such as RAM, a hard drive, CD, smart card, 3.5" diskette, etc., for performing the functions disclosed herein and to achieve a technical effect in accordance with the disclosure.

The laser proton acceleration system 06 may be simulated using a simulator 120 having a processor 122 and a computer readable medium 124. The processor executes a simulator module 126 described further below. The simulator module includes a series of programmable instructions capable of being executed by the processor 122. The series of programmable instructions can be stored on computer-readable medium 124 accessible by the processor 122, such as RAM, a hard drive, CD, smart card, 3.5" diskette, etc., for performing the functions disclosed herein and to achieve a technical effect in accordance with the disclosure.

As shown in FIGS. 2-3, each treatment room 102 is provided with a target 104 formed of foil which is irradiated by the laser beam 02 and transformed into plasma having a target density. Protons in the target 104 are accelerated for producing treatment energy directed at an object for treating the object with the treatment energy.

When the objective is to produce monoenergetic proton energy, the target 104 is selected to have particular parameters and characteristics for achieving the generation of monoenergetic energy. For example, as described in greater detail below, to achieve monoenergetic energy generation the target density of the target's 104 foil is greater than critical density, and the foil has an optimal thickness that is less than the laser beam's wavelength and is selected as a function of the laser beam intensity, laser beam wavelength, and target density.

This combination of parameters is designed to achieve radiation pressure acceleration (RPA) and to balance a ponderomotive force of the laser beam radiation accelerating electrons in the foil with a space charge force due to the electric field produced due to the space charge separation of ion and electrons pulling the electrons back. Thus, when the laser beam, after redirection, impacts a front surface of the foil, a first electron layer is formed at the rear surface of the foil by electrons pushed by the ponderomotive force of the laser beam and a second electron layer is formed at the front surface of the foil by electrons swept by the space charge force. The first and second layers are stable because the ponderomotive force is balanced by the space charge force. Protons are trapped between the first and second layers. The double layer with the trapped protons is accelerated as a whole by laser radiation, achieving an acceleration gradient in the order of 100-1000 GV/cm for achieving monoenergetic treatment energy in the order of 50-350 MeV.

The laser delivery system 100 further may include one or more reflecting mirrors 04 associated with each treatment room 102. The steering mirror 03 directs the laser beam 02 to impact the reflecting mirror 04 that is associated with a selected treatment room 102. The reflecting mirror 04 that is associated with the selected treatment room 102 is impacted by the laser beam 02 and directs the redirected laser beam 05 either to the target 104 associated with the selected treatment room 102 or to a reflection mirror of a set of one or more reflection mirrors that is associated with the selected treatment room 102. In the example shown in FIG. 3, the set of reflection mirrors includes a first and second reflection mirror 12 and 13, respectively. The associated reflecting mirror 04 directs the redirected laser beam 05 to the first reflection mirror 12. The first reflection mirror 12 directs the redirected laser beam 05 to the second reflection mirror 13 which redirects the laser beam 05 to the target 104 of the laser proton acceleration system 06.

The laser beam 05 impacts the target 104. When the target 104 and the laser beam 05 have selected properties and characteristics (as described further above and below), protons are accelerated by RPA to generate efficient treatment monoenergy. The monoenergy, or monoenergetic ions, are channeled by the energy delivery nozzle 11 to an object to be treated by the energy generated. In the example shown in FIGS. 2 and 3, the object to be treated by the energy is a human patient positioned in a gantry 10. The patient is positioned at patient position 08 on a robotic couch 09 positioned within the gantry 10. The gantry 10 and/or the robotic couch 09 may be rotatable around a longitudinal axis 108. Furthermore, the robotic couch 09 may be translated for moving along the x-, y-, and z-axes, including forwards and backwards as shown by arrow 110, up and down, or right and left. The rotation of the compact gantry 10 allows the laser proton acceleration system 06 to rotate with the gantry 10 360 degree around the patient. Alternatively, the laser proton acceleration system 06 can rotate around 360 degrees around the gantry 10 along.

The energy delivery nozzle 11 can be positioned in at least two different positions, designated as 11a and 11b, respectively, by rotating the energy delivery nozzle 11. In the example shown, the energy delivery nozzle 11 can rotate up to 15° in either direction about an axis parallel to axis 108. The ability to rotate the energy delivery nozzle 11 allows the operator to aim the treatment energy at a desired area on the patient, giving the operator greater control at aiming the energy effectively. Accordingly, the beam delivery nozzle 11 is designed to rotate within 15° forward along gantry 10 in the rotating axis direction and perpendicular to the gantry's 10 rotation direction. The movement of the couch 09, gantry 10, and nozzle 11 are all provided by mechanical means that can be controlled by controller 12. The ability to controllably move the couch 09, gantry 10, and nozzle 11 as described above allows for a comprehensive coverage of the patient's body for treatment thereof. In this way the treatment energy can be aimed at a direction required by various medical applications.

When the treatment energy is used for treating cancer, for example, the energy can be directed more accurately at a tumor without irradiating nearby sensitive organs.

Since the RPA of the double layer as a whole provides a large acceleration gradient, a large amount of energy can be generated without consuming much space, allowing for a compact laser delivery system 100, and particularly a compact laser proton acceleration system 06. The distance from the second reflection mirror 12 to the area on the patient that is being treated with the treatment energy can be less than 3 meters.

Figure 4:
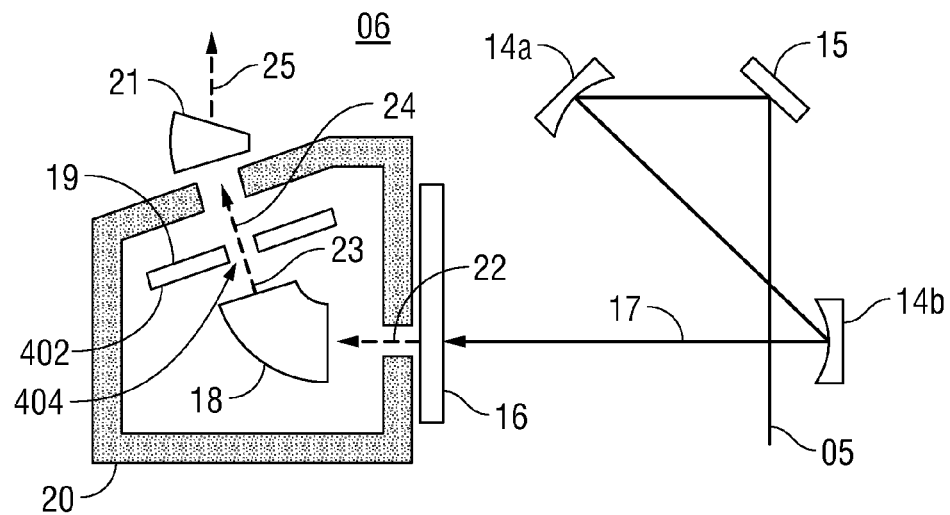
FIG. 4 is a schematic illustration of a laser proton acceleration system in accordance with the present disclosure.

FIG. 4 shows the laser proton system acceleration 06. The laser proton acceleration system 06 is provided with an interior reflection mirror 15 that is impacted by the laser beam 05 redirected from the second reflection mirror 12. The laser target interaction can be complicated by the presence of an amplified spontaneous emission (ASE pedestal) at a leading edge of the high-intensity laser pulse. An ASE pedestal can cause target expansion and pre-plasma formation and reduce the efficiency of the RPA acceleration. For achieving monoenergetic protons the laser beam 05 is characterized by a high contrast ratio, defined as the main-pulse-to-ASE intensity contrast ratio, preferably $10^9 \sim 10^{11}$. Interior reflection mirror 15 redirects the laser beam to a first mirror shaper 14a which redirects the laser beam to a second mirror shaper 14b. The first and second mirror shapers 14a, b shape or tailor the laser beam to produce a shaped and focused laser pulse 17 in accordance with a selected laser beam profile design.

The first and second mirror shapers 14a, b are shaped, sized, and mounted to achieve the desired laser beam profile design. The number of mirror shapers is not limited to two, but can be selected to achieve the desired laser beam profile design. A variety of different shapes and/or sizes of mirror shapers and mounting positions may be provided. A mounting apparatus 506 is provided to position the mirror shapers. The mounting apparatus 506 may be adjustable and controlled by the controller 112. The controller 112 may select which mirror shapers of the variety provided should be used for shaping and focusing the laser beam for a treatment session to achieve a desired laser beam profile. The controller 112 may then control the mounting apparatus 506 to position the selected mirror shapers so that they are in the path of the laser beam for shaping and focusing the laser beam and or affecting the path of the laser beam. The unselected mirror shapers will be positioned by the mounting apparatus 506 outside of the path of the laser beam in order not to affect the shape or path of the laser beam.

Figure 5:
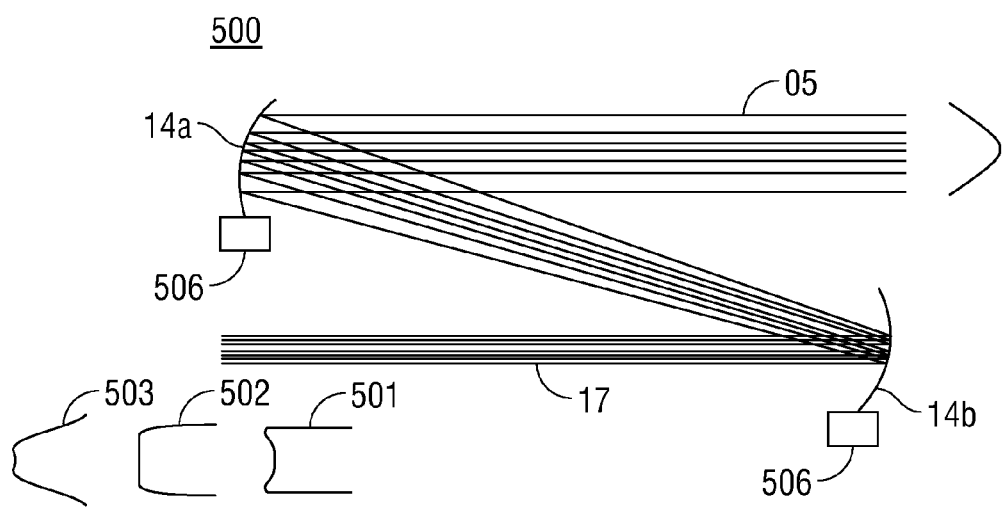
FIG. 5 is a schematic view of a beam reshaping system in accordance with the present disclosure.

FIG. 5 shows a beam reshaping system 500 for reshaping and focusing the laser beam 05, including the first and second mirror shapers 14a, b. Profile designs for laser beam 17 achieved by shaping laser beam 05 using the first and second mirror shapers 14a,b are shown as first, second, and third radial laser beam intensity profile designs 501 (double super-Gaussian), 502 (flat top), and 503 (double Gaussian), respectively. Using the laser beam profile as described above can help trap electrons around the beam axis along the laser propagation direction during the acceleration, delay the target from becoming transparent to the laser, and therefore maintain continuous radiation pressure acceleration of the foil.

Figure 6:
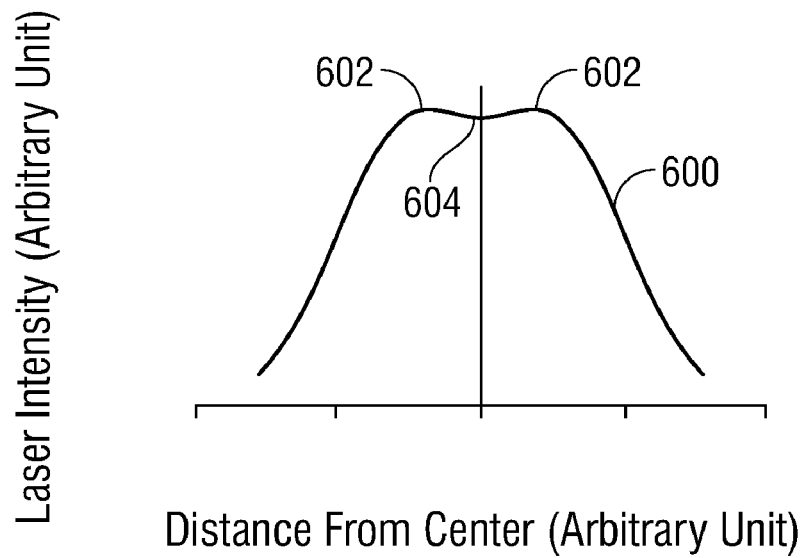
FIG. 6 is a radial amplitude profile of a profile design of a shaped laser beam.

FIG. 6 shows the radial amplitude profile of the third profile design, 503. Curve 600 shows the profile of the normalized radial amplitude of the laser beam. The first and second mirror shapers 14a, b shape the laser beam to have two peaks 602 of normalized amplitude $A_{NP}$. In one example, a period spans twenty laser wavelengths, with an interval of eight or less wavelengths between the two peaks 602. A trough 604 located between the two peaks 602 has amplitude $A_{NT}$, where $A_{NT}<0.9A_{NP}$. The shaped laser beam confines energized particles around the laser beam axis along the laser propagation direction and assists in trapping the particles. Thus the electrons are trapped within a small radial distance around the z-axis. Furthermore, for a laser beam of Gaussian profile, when the impact surface of the target 104 is designed with a convex shape, the shape can compensate for the Gaussian distribution of the laser intensity in the radial direction. This compensation is intended for use with a regular Gaussian beam. But, with a larger amount of electrons near the axis for the convex target, it can also be used with other beam profiles for better trapping of electrons around the axis along z-direction.

The controller 112 may include a plurality of distributed controllers for controlling the system parameters as described. The controller module 116 may include sub-modules that are distributed for executing on processors associated with the distributed controllers, or the controller module 116 may be centralized for centralized operation of the distributed controllers. The controller 112 may select and control parameters of the laser source, including controlling its intensity, time profile, beam width, pre-pulse, and contrast ratio for generating the desired treatment energy. The controller 112 may further select parameters of the target 104 for generating the desired treatment energy, including selecting the optimal thickness of the target 104, as described further below. The controller 112 may control the positioning of the steering mirror 03 for selecting and controlling which treatment room 102 will receive the laser beam 05. The controller may control the energy delivery nozzle 11 and the robotic couch 09 for selecting and controlling their respective positions. The controller 112 further may control the various mirrors used for redirecting, shaping and focusing the laser beam. The controller 112 may also control the flow of current to a solenoid for generating an adjustable magnetic field that confines electrons of the target 104. The controller 112 may also control the flow of current to coils of various magnets for steering a generated particle beam and controlling properties of the particle beam.

Figure 12:
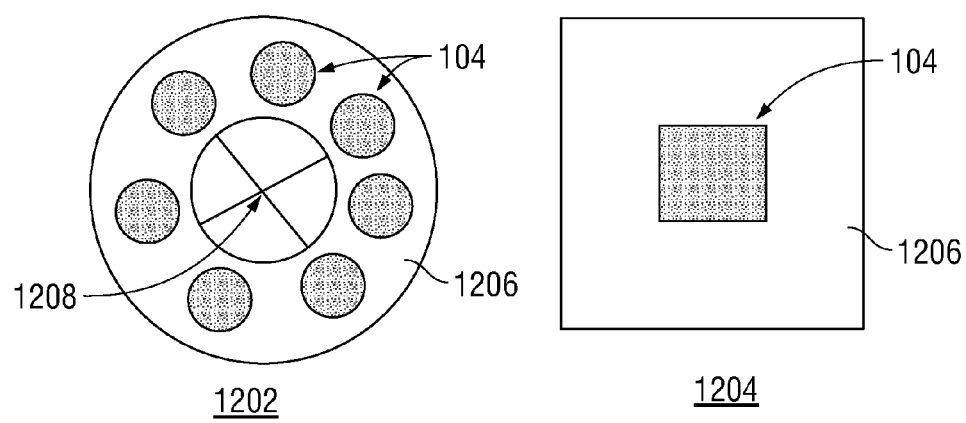
FIG. 12 shows two configurations of a target cartridge of the laser proton acceleration system.

The reshaped and focused laser pulse 17 impacts the target 104, or a selected target 104, that is held by a target cartridge configured as target cartridge 1202 or 1204 shown in FIG. 12. The target 104 (or selected target 104) lies in an x-y plane and laser pulse 17 travels in a longitudinal direction along an azimuthal axis along the z-direction which is normal to the x-y plane. The laser travels in a longitudinal direction along in the z-direction which is normal to the x-y plane of the target. Each of the target cartridges includes a frame 1206 that holds one or more targets 104. The frame 1206 of target cartridge 1204 holds a single target 104. The target cartridge 1204 and target 104 are positioned so that the target 104 is impacted by laser pulse 17.

The frame 1206 of target cartridge 1202 holds a plurality of targets 104. The target cartridge 1202 is rotatable around an axis 1208. The target cartridge 1202 is rotated so that a selected target 104 of the plurality of targets 104 is impacted by laser pulse 17. The rotation of the rotation of the target cartridge 1202 is controlled by the controller 112.

Each target 104 of the plurality of targets 104 has a target design and different target designs may be used for each of the plurality of targets. As discussed further below, the target design may include characteristics or parameters such as the thickness of the target's 104 foil, the shape of the impact face of the target 104, and the density of the target 104. Accordingly, the controller 112 may rotate the target cartridge 1202 to select a target 104 that has a selected target design. Other configurations are envisioned of a target cartridge that can be manipulated by the controller 112 to select a target 104 from a plurality of targets that has a selected target design, and the disclosure is not limited to the configuration of target cartridge 1202 shown.

Energetic particle beam 22 is generated from the target due to the RPA and enters radiation shielding block 20 through an aperture. The energetic particle beam 22 is received by high field bending magnet 18 which acts on the particle beam 22 to bend particles having different energies with a different respective radius. Particle beam 23 is output from magnet 18 and is filtered as it travels through energy selection slot 19.

By controlling the magnetic field strength produced from the bending magnet 18, the gyro-radius for particle beam 23 can be controlled so that only particles of desired energy are allowed to pass through the energy selection filter 19. Therefore, the energy spread and beam spot size of filtered energetic particle beam 24 is controlled. An example of this control is controlling the profile of the filtered particle beam 24 by controlling the particle energy spread ratio of the filtered particle beam 24, defined as $\Delta E/E$, where $\Delta E$ is the particle energy spread, and E is principle particle beam energy. The particle energy spread ratio $\Delta E/E$ is selectable within the range of 1 to 10 percent or 0.01 to 0.1. The beam spot size may be selected to range from the size of tens of microns to sub-millimeter in accordance with the requirements of the treatment that the treatment energy is used for, e.g. the requirements of a particular medical use.

Selection slot 19 is formed of movable plates 402. Gap 404 is formed between the plates 402 and the filtered particle beam 24 passes through the gap 404. By moving the plates 402 to adjust the size of the gap 404 the particle energy spread ratio is controlled. Accordingly, controller 112 can control the movement of the plates 402 to control the profile of the filtered particle beam 24, including its particle energy spread ratio. Selection slot 19 allows the part of the particle beam 24 that has a selected energy intensity to pass through the gap 404 of energy selection slot 19 and allows particles with an undesired higher or lower energy intensity than the selected energy intensity to hit the plates 402 of selection slot 19.

The size of the particle beam spot of particle beam 24 can be controlled by adjusting the gap size 404 together with the magnetic field strength produced by magnet 18. To adjust the gap size 404, the position of plate 402 of slot 19 can be adjusted or the entire slot 19 can be replaced with different gap size as needed by the application. As an example, a magnet 18 with magnetic field strength=5 Tesla, used for producing a 100 MeV proton beam 24 with 1 percent energy spread, the gap distance needed is 1 mm and the resulting beam spot radius is 0.5 mm. A magnet 18 with magnetic field strength=8.5 Tesla, for producing a 100 MeV proton beam with 1 percent energy spread, the gap distance needed is 0.6 mm, and the resulting beam spot radius is 0.3 mm.

The bending magnets 18 and 21 can be formed as a dipole magnet made of ferromagnetic-core electromagnets with iron core providing magnetic field up to 2 Tesla. Magnet 18 can be configured like magnets 2600 and 2601 shown in FIG. 26. Magnets 2600 and 2601 alternatively have a core 2602, and superconducting coils 2604 which provide a stronger and adjustable magnetic field 2606. Two alternative embodiments 2600 and 2601 of magnet 18 are shown. The current in the coils 2604, which controls the strength of the magnetic field 2606, of bending magnet is controlled by controller 112. Accordingly, the controller 112 can control the current in the coils 2604, which controls the strength of the magnetic field 2606, which together with the size of gap 404 controls the energy spread and beam spot radius of particle beam 24. In the case of superconducting magnet, the coils of magnet can be made of super conductor material: NbTi, or Nb3Sn, or High-Temperature Super-Conductor (HTSC) YBaCuO, or combined layers of coils made of these three materials.

The filtered particle beam 24 exits the radiation shielding block 20 via another aperture and passes through final steering bending magnet 21. It is guided by the final steering bending magnet 21 and exits the steering bending magnet 21 as a low emittance particle beam 25 which is guided by the magnet 21 to beam delivery nozzle 11. The steering bending magnet 21 provides the ability to steer the particle beam 25 and to select the angle at which the particle beam 25 is incident to the patient's body. Accordingly, the angle at which the particle beam 25 is incident to the patient's body selectable and is not limited to a 90 degree angle or a normal incidence direction relative to the patient's body.

Figure 26:
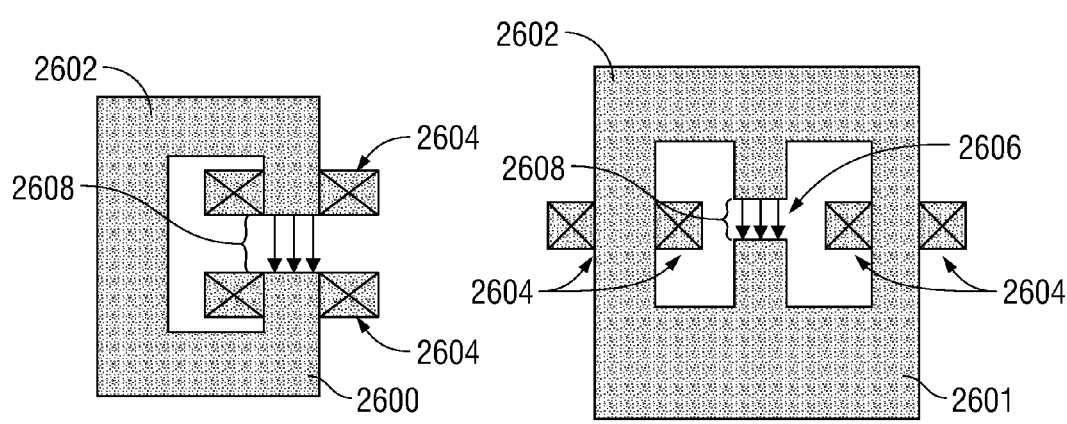
FIG. 26 is a schematic illustration of different embodiments of bending magnets used in the laser proton acceleration system.

Like magnet 18, the bending magnet 21 can be made of ferromagnetic-core electromagnets with iron core providing magnetic field up to 2 Tesla. Magnet 21 can alternatively be formed as magnets 2600 and 2601 as shown in FIG. 26, magnet 21 can alternatively be made with core 2602 and superconducting coils 2604 providing a stronger and adjustable magnetic field 2606 in accordance with embodiment 2600 or 2601. Controller 112 is used to control the current in the coil 2604 of magnet 21 and subsequently to control the magnetic field strength of bending magnet 21. The superconducting coils 2604 of magnet 21 can be made of super conductor material: NbTi, or Nb3Sn, or High-Temperature Super-Conductor (HTSC) YBaCuO, or combined layers of coils made of these three materials.

The particle beam 25 is bended in gap 2608 of dipole magnet 21. Without applying current, the magnetic field is zero and the particle beam 25 exits shielding block 20 at an angle normal to the shielding block 20. As an example, by applying magnetic field=1 Tesla, over a distance of 25 cm normal to the shielding block 20, the particle beam 25 can bend by about 15 degree and exit at a 75 degree to the shielding block 20.

Nozzle 11 is configured to swing perpendicular to the gantry rotation direction. The ability to swing the nozzle 11 combined with the ability to control the angle of incidence of particle beam 25 provides for the ability to select the treatment angle which is the angle at which the particle beam 25 is incident to the patient's body for irradiating it Reducing the magnetic field of final steering magnet 21 causes the particle beam 25 to bend at a smaller angle for directing the particle beam 25 through the nozzle 11 when it is positioned in position 11a (see FIG. 2). Increasing the magnetic field strength of the final steering magnet 21 causes the particle beam 25 to bend at a larger angle for directing the particle beam 25 through the nozzle 11 when it is positioned in position 11b. The energy flux and spot size properties of the particle beam 25 are not affected by the final steering magnet 21 and are the same as for the particle beam 24 before it passed through the final steering magnet 21.

Figure 7:
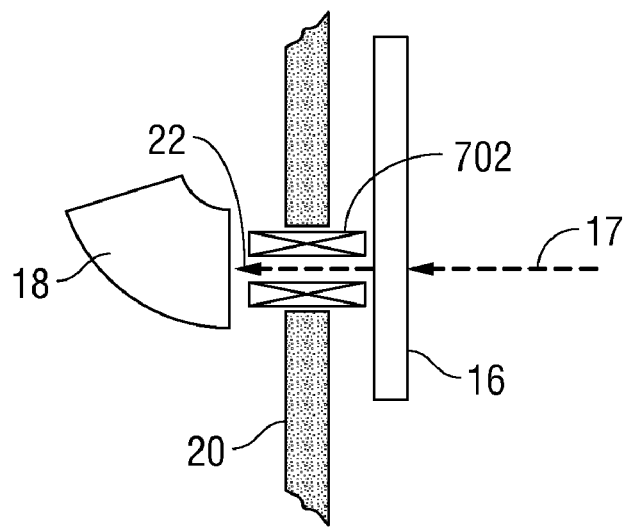
FIG. 7 is an enlarged view of a portion of the laser proton acceleration system including an external solenoid.

FIG. 7 shows an optional external cylindrical current loop (solenoid) 702 for producing a magnetic guiding field. Solenoid 702 produces an axial magnetic field along the direction of laser propagation that acts on energetic particle beam 22 before it is affected by bending magnet 18. This axial magnetic field confines the electrons around the axial axis. Confining the electrons around the axis with external axial magnetic field stabilizes the electron-ion double layer and maintains the radiation pressure acceleration of the double layer.

Figure 17:
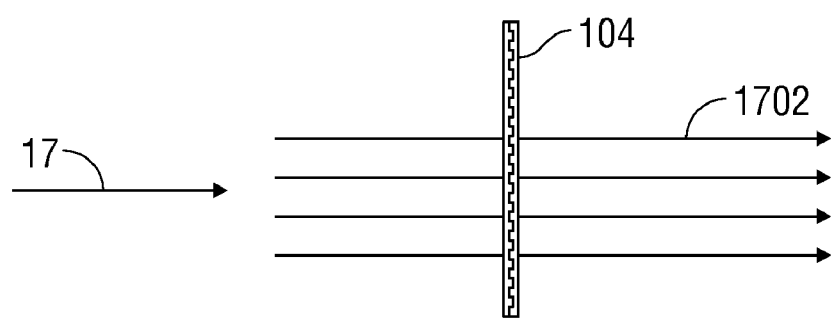
FIG. 17 shows an external magnetic guiding field generated by the solenoid shown in FIG. 7.

With reference to FIG. 17, solenoid 702 applies a magnetic guiding field whose strength affects the intensity of the energy of the particle beam 22. The strength of the magnetic guiding field of solenoid 702 is selectable by controlling the current in the coils of solenoid. The coils inside solenoid 702 can be made of super conductor material: NbTi, or Nb3Sn, or HTSC (YBaCuO), or combined layers of coils made of these three materials. The controller 112 controls the current in the coil and subsequently strength of the axial magnetic field. Solenoid 702 guides the beam particle 22 to selection slot 19.

Reference to laser beams 02 and 05 as well as reference to laser pulse 17 and particle beams 22, 23, 24, 25 refer to different stages of the laser beam as it is redirected, shaped, and transformed into a particle beam that is further filtered and bent to produce desirable treatment energy represented as particle beam 25.

2. Laser Radiative Pressure on Over-Dense Plasma

In this section the ponderomotive pressure of a relativistic intensity laser in an over-dense plasma is derived and its relation to the usual radiation pressure is demonstrated. The laser power is directly related to the ponderomotive force of the acceleration, which further determines the acceleration gradient, and in turn determines the particle energy upon being accelerated. This makes the particle energy tunable by tuning the incident laser power, such as by controlling power pumped to the laser source 01. The ponderomotive force in the current example is the dominant interaction of laser with plasma.

A circular polarized laser is used. Linearly polarized light is less suitable because it may lead to chaotic heating of the electrons. The circularly polarized laser light is important for the ponderomotive force to be dominant and for electron acceleration to be unidirectional along laser propagation. Circular polarization may also be important for radial confinement of electrons in two dimensions by producing a magnetic field via an inverse Faraday Effect. For conservation of angular momentum, the incident and reflected light may impart an angular momentum to electrons, providing a current source for an axial magnetic field to confine electrons in the radial direction.

Plasma is over-dense when the plasma has a density greater than the critical density. The critical density is defined as $n_c = \epsilon_0 m_e^2 \omega_0^2/e^2$, where $\epsilon_0$ is the dielectric constant, $m_e$ and e are electron mass and charge, respectively. $\omega_0$ is the laser angular frequency. It is a function of laser properties. If the plasma density is lower than the critical density, the plasma is transparent to the laser.

A circularly polarized laser is used having incidental energy:

$$\overline{E}_i = i\overline{B}_i = (\hat{x}+i\hat{y})A_0 e^{-i(\omega t - \omega z/c)}, \tag{1}$$

where:
i is $e^{i\pi/2}$, a phase difference in producing circular polarization;
$\overline{B}_i$ is the input magnetic field;
$\hat{x}$ and $\hat{y}$ are the unit vectors along the x and y directions;
$A_0$ is the linear polarized amplitude of the input EM wave;
−e is the electronic charge;
c is the speed of light in vacuum; and
$\omega$ is the laser frequency multiplied by $2\pi$ The energy $\overline{E}_i$ is normally incident to an overdense plasma slab (for z>0, where +z is the direction of input laser radiation, and where the laser beam first hits the front surface or impact surface of the foil at z=0)) of density $n_0$. The fields of the reflected wave (z<0) are:

$$\overline{E}_R = -i\overline{B}_R = (\hat{x}+i\hat{y})RA_0 e^{-i(\omega t + \omega z/c)}. \tag{2}$$

where:
$\overline{B}_R$ is the reflected magnetic field; and
R is reflection coefficient;

Solving the transmitted wave amplitude $A_T$, generally evanescent, and phase, for z>0, $$\overline{E}_T = (\hat{x}+i\hat{y})A_T(z)e^{-i\omega t}, \tag{3}$$

$$\overline{B}_T = -(\hat{x}+i\hat{y})\frac{c}{\omega}\frac{\partial A_T}{\partial z} e^{-i\omega t}.$$

The cold plasma dielectric function is used with relativistic mass modification by the ponderomotive force:

$$\varepsilon = 1 - \frac{\omega_p^2}{\omega^2}\frac{n_e}{n_0}\frac{1}{(1+a_T^2)^{1/2}} < 0,$$

where normalized transmitted electric field amplitude $$a_T = \frac{e|A_T|}{m\omega c},$$

electron plasma frequency $\omega_p = (4\pi n_0 e^2/m)^{1/2}$, where m, and $n_e$ are the mass and density of the electrons, the transmitted field is evanescent, e.g., $A_T = |A_T|\exp(i\phi_0)$, with $\phi_0$ a constant determined by the continuity conditions at z=0, and $|A_T|$ a monotonically decreasing function of z. $\omega_p^2$ is the square of the plasma frequency, where plasma frequency is a function of the plasma density. $a_T$ is the normalized amplitude of electric field transmitted into the electron layer formed at the rear end of the target.

The continuity of tangential components of fields at z=0 gives:

$$(1+R)a_0 = a_T(0)e^{i\phi_0}, \tag{4}$$

$$(1-R)a_0 = \frac{c}{i\omega}\frac{da_T}{dz}\bigg|_0 e^{i\phi_0},$$

leading to $$a_T(0) + \frac{c}{i\omega}\frac{da_T}{dz}\bigg|_0 = 2a_0 e^{-i\phi_0},$$

or $$a_T(0) = 2a_0\cos\phi_0, \quad \frac{da_T}{dz}\bigg|_0 = 2a_0\sin\phi_0, \tag{5}$$

$$a_T^2(0) + \frac{c^2}{\omega^2}\left(\frac{da_T}{dz}\bigg|_0\right)^2 = 4a_0^2,$$

where normalized incident laser electric field amplitude $$a_0 = \frac{eA_0}{m\omega c}.$$

The wave equation governing $a_T$ is:

$$\frac{d^2 a_T}{dz^2} - \frac{\omega^2}{c^2}\left[\frac{\omega_p^2}{\omega^2}\frac{n_e}{n_0}\frac{1}{(1+a_T^2)^{1/2}} - 1\right]a_T = 0. \tag{6}$$

Initially, the density modification may be ignored so that ($n_e = n_0$), where $n_0$ is the initial electron number density of the target, and Equation (6) is integrated, giving:

$$\frac{da_T}{dz} = -\left[\frac{2\omega_p^2}{c^2}[(1+a_T^2)^{1/2}-1] - \frac{\omega^2}{c^2}a_T^2\right]^{1/2}, \tag{7}$$

with z→∞, $a_T$→0, $$\frac{da_T}{dz} \to 0.$$

From Equations (5) and (7):

$$a_T(0) = 2\frac{\omega}{\omega_p}a_0\left(1 + \frac{\omega^2}{\omega_p^2}a_0^2\right)^{1/2}. \tag{8}$$

In the limit of $$\frac{\omega}{\omega_p}a_0 \gg 1, \quad a_T(0) = 2\frac{\omega^2}{\omega_p^2}a_0^2 > 1.$$

The spatial variation of density $n_e$ is taken into account by using the force balance on electrons $eE_s = \partial/\partial z(e\phi_P)$ in the entire sheath region, where $\phi_P$ is the ponderomotive potential in the entire electron sheath region in which the electron number density is nonzero. The Poisson's equation $\partial E_s/\partial z = 4\pi e(n_0 - n_e)$ is used to obtain $$\frac{n_e}{n_0} = 1 + \frac{c^2}{\omega_p^2} \frac{\partial^2}{\partial z^2}(1+a_T^2)^{1/2},$$

which on using Equation (6) gives:

$$\frac{n_e}{n_0} = 1 + a_T^2 + \frac{c^2}{\omega_p^2} \frac{1}{\sqrt{1+a_T^2}} \left(\frac{\partial a_T}{\partial z}\right)^2 - \frac{\omega^2}{\omega_p^2} a_T^2 (1+a_T^2)^{1/2}. \quad (9)$$

Figure 8:
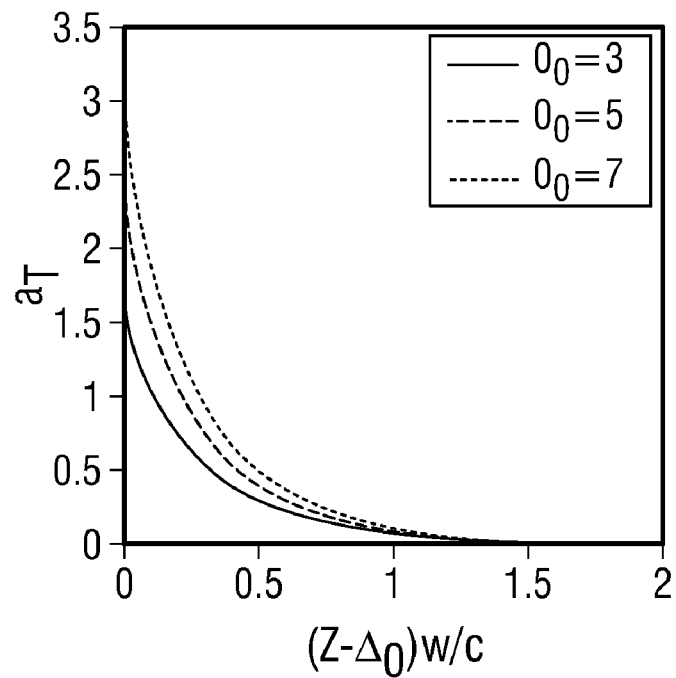
FIG. 8 is a plot of the distribution of a normalized transmitted field amplitude vs. z for different cases of $a_0$ and $\omega_p^2/\omega^2$.
Figure 8:
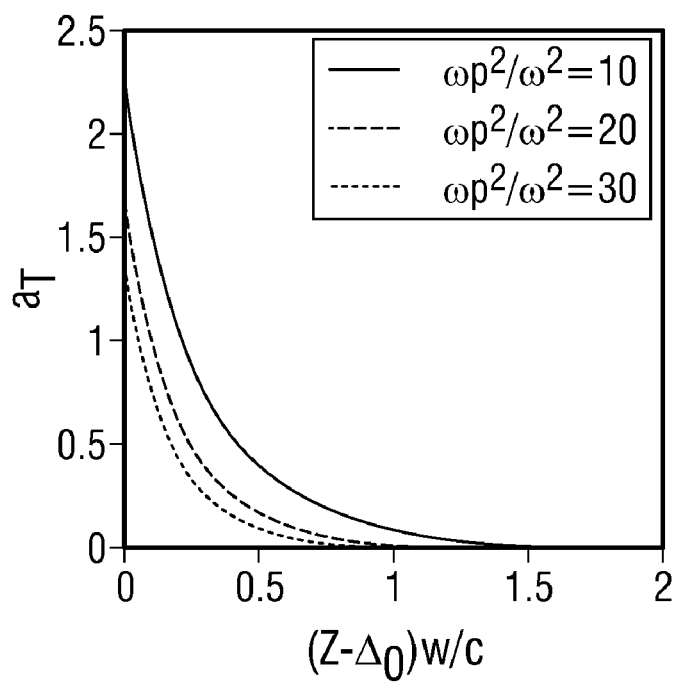

FIG. 8 shows solutions of Equations (6) and (9) for different cases of $a_0$ and $\omega_p^2/\omega^2$, illustrating distribution of normalized transmitted field amplitude vs. Z. Graph 802 shows three curves for which $\omega_p^2/\omega^2 = 10$, the three curves corresponding to $a_0 = 3, 5, 7$, respectively. Graph 804 shows three curves for which $a_0 = 5$, the three curves corresponding to $\omega_p^2/\omega^2 = 10, 20, 30$, respectively. At higher initial amplitude, the transmitted amplitude is larger, however its decay with distance is faster. On increasing the plasma density, the transmitted amplitude falls down. Of note is that $a_T(0)$ is less than $a_0$.

The ponderomotive potential is determined as follows: $\phi_P = -(mc^2/e)[(1+a_T^2)^{1/2}-1]$. The ponderomotive force is then:

$$F_P = e\frac{\partial \phi_P}{\partial z} = -\frac{mc^2 a_T}{(1+a_T^2)^{1/2}} \frac{\partial a_T}{\partial z}. \quad (10)$$

The ponderomotive force is at a maximum at $z=0$ and falls off over a scale length $\sim c/\omega_p$. If the ponderomotive force on all the electrons per unit x-y cross-section of the plasma is integrated and Equation (8) is used, the result is:

$$F = \int_0^\infty F_P n_0 dz = 2n_0 mc^2 a_0^2 \frac{\omega^2}{\omega_p^2} = 2I_0/c; \quad (11)$$

where $I_0$ is the incident laser intensity. F substantially equals the momentum change per unit area of the incident laser, i.e., radiation pressure when reflectivity is 100%. This demonstrates that the origin of the ponderomotive force for direct acceleration of electron layer is from laser radiation pressure. Therefore, by tuning the laser power, the acceleration gradient of the RPA and the resulting energy of monoenergetic protons are controlled.

3. Optimal Target Thickness

An ultra-thin (submicron) target is desired. The optimal thickness $D = \Delta_s$ is the thickness at which the acceleration of the electron sheath nearly vanishes. The ponderomotive force pushes the electrons forward leaving behind a positive ion space charge and piling up electrons at the laser front into a sheath of width $l_s \sim c/\omega_p$. As the laser front moves a distance $\Delta$, the electron density in the sheath can be approximately written as $n_e \approx n_0(1+\Delta/l_s)$ and the space charge field at $z=\Delta$, where z lies along the laser propagation direction, is $\bar{E}_s = \hat{z} 4\pi n_0 e\Delta$; $\bar{E}_s(\Delta)$ increases with $\Delta$. At $\Delta = \Delta_s$ where space charge force at $z=\Delta_s$ balances the ponderomotive force: $eE_s = F_p(\Delta_s)$ on electrons. Using Equation (8) and the Poisson Equation above:

$$\Delta_s = -\frac{c^2}{\omega_p^2} \frac{a_T(\Delta_s)}{(1+a_T^2(\Delta_s))^{1/2}} \left(\frac{\partial a_T}{\partial z}\right) \Delta_s \quad (12)$$

$$= \frac{c}{\omega_p} \frac{\omega}{\omega_p} \frac{a_T(\Delta_s)}{(1+a_T^2(\Delta_s))^{1/2}} (4a_0^2 - a_T^2(\Delta_s))^{1/2}.$$

where $a_T(\Delta_s)$ and $$\left(\frac{\partial a_T}{\partial z}\right) \Delta_s$$

are the same as $a_T(0)$ and $$\left(\frac{\partial a_T}{\partial z}\right)_0$$

given by Equations (7) and (8). In the limit of $a_0 > a_T \gg 1$, $$\Delta_s \approx \frac{4\pi}{\lambda_L}\left(\frac{c}{\omega_p}\right)^2 a_0 = \frac{\lambda_L}{\pi}\left(\frac{\omega}{\omega_p}\right)^2 a_0.$$

To avoid hole boring, also known as wave tunneling, $\Delta_s > c/\omega_p$ or $2a_0 \omega/\omega_p > 1$. For the electrostatic field to be greater than the laser field, $$\frac{\omega_p^2}{\omega^2} > a_0$$

is also required. So, there is a range of $a_0$ for this scheme to work, $$\frac{\omega_p^2}{\omega^2} > a_0 > \frac{\omega_p}{2\omega}.$$

In conclusion, Optimal thickness is a function of the laser intensity, laser wavelength (or frequency), and target density (or plasma frequency).

For $a_0 = 5$, $\omega_p^2/\omega^2 = 10$, optimum foil thickness $D = \Delta_s = 0.16 \lambda_L$. If the thickness of the thin foil, D, is equal to $\Delta_s$, a compressed electron layer will be formed at the rear surface, which's electrical field will attract the ions to within its skin depth. The electron sheath is simply detached from the bulk ions and moves out in vacuum, trapping the ions within its width~skin depth. The ions are confined by the inertial force of their acceleration; together with the electron sheath, they form a double layer. This double layer is accelerated by the laser ponderomotive force or radiation pressure as demonstrated below.

Accordingly, the optimal thickness $\Delta_s$ is: In the limit of $a_0 > a_T \gg 1$, $$\Delta_s \approx \frac{4\pi}{\lambda_L}\left(\frac{c}{\omega_p}\right)^2 a_0 = \frac{\lambda_L}{\pi}\left(\frac{\omega}{\omega_p}\right)^2 a_0,$$

with $$\frac{\omega_p^2}{\omega^2} > a_0 > \frac{\omega_p}{2\omega}.$$

Monoenergetic particles can still be obtained, but with less efficiency, i.e. with less energy given the same laser beam profile, when the target thickness is configured within a factor of 2 of $\Delta_s$. Even better results can be obtained for a target thickness that has a range within a factor of 1-1.5 of $\Delta_s$.

4. Self-Organized Double-Layer Formation and Ion Trapping

The foil is irradiated by an intense laser light that completely ionizes the foil to form a slab of plasma, and pushes the electrons forward towards the rear front end of the plasma slab by the radiation pressure, which is the integrated ponderomotive force for all electrons. A stable electron layer is formed at the rear surface at $z=\Delta_s$, where the ponderomotive force is balanced by the electrostatic force due to the ions left behind.

Since the foil thickness corresponds to the maximum space charge field (the electric field due to the charge separation of ion and electron) at the front edge of the foil due to electrons being swept there and there is a balance of the ponderomotive force and the ions electric force, the electron layer is trapped. Protons are accelerated by the electrostatic field of these trapped electrons, but are held back by the inertial force of the accelerating frame. The total potential, summation of electrostatic potential and acceleration potential, has a minimum which traps ions in the accelerated frame. An accelerated frame is the reference frame that follows the center of mass of the foil. Since the foil is actually accelerated by the beam, all the particles in this frame feel an inertia force $-ma$, where a is the acceleration vector of the foil. Thus, a large portion of ions, e.g., 80%, are trapped by the balance of the electric force of the electrons and the inertia force of the accelerating foil. A self-organized double layer is thus formed and retains its stability in the plasma state, with density higher than solid state density and effective temperature of the order of ponderomotive potential of the electrons in the laser field.

Figure 9:
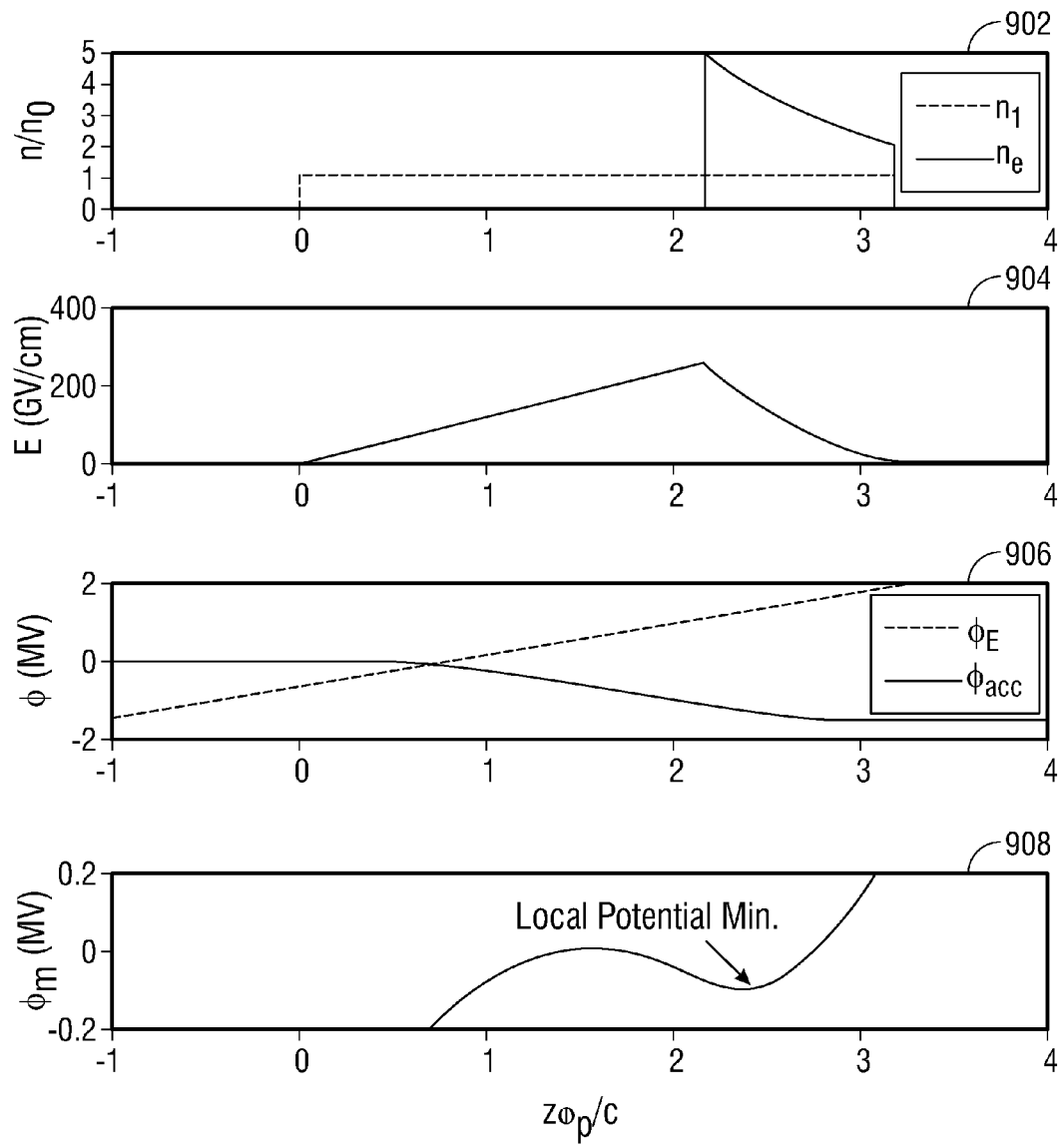
FIG. 9 shows a series of plots illustrating self-organization of a double layer with a layer of trapped ions formed in a target of the laser proton acceleration system.

FIG. 9 illustrates the self-organization of the double layer with the layer of trapped ions. From the transmitted wave amplitude versus z illustrated in FIG. 8, the electron density distribution inside the electron sheath can be derived using Equation (9), as shown in panel 902 together with the unperturbed background ion density. Panel 904 shows the spatial distribution of the electric field E solved from the Poisson equation. Panel 906 shows electrostatic potential $\phi_E$ and acceleration potential. Panel 908 shows the effective/total potential in the accelerated frame as functions of z, for $\omega_p^2/\omega^2=10$ and $a_0=5$. The electric potential decreases monotonically. On the other hand, the ions experience an inertial force $-mdV/dt$ due to the acceleration of the target by the ponderomotive force, which tends to confine them by reflecting them back to the rear surface. The potential well of $\phi_{tot}=\phi_E+\phi_{acc}$, where $$\phi_{acc} = \frac{m_i}{e}\left(\frac{dV}{dt}\right)z,$$

is shown in panel 908.

These ions can now be stably trapped in the well formed by the combined forces of the electron sheath and the inertial force of the accelerated frame, where the well is a very thin layer along the z-direction. Together, they form the double layer, which is accelerated by the laser radiation pressure. Target thickness $D=\Delta_s$, where electron experiences force balance, is important for the double layer formation, putting the ions into the trap.

5. Acceleration of the Moving Double Layer with Trapped Protons

The laser radiation pressure can accelerate the double layer, trapping the protons in it by high energy with narrow energy spread. The accelerating gradient can be several MeV per micron or higher, which is a thousand times higher than the usual linear laser accelerator. The double layer is accelerated as a whole by the radiative acceleration, thus the whole thin foil is transformed into a double layer. The protons trapped in the double layer can be accelerated to a high energy with a narrow bandwidth.

Energetic particle produced from laser proton accelerator have energy spread and it is defined that the monoenergetic particle beam has a ratio between energy spread of full-width half maximum particle flux to the energy of maximum energy flux is within 10 percent or 0.1. The energies achieved using RPA are one order of magnitude higher than the equivalent energies obtained by Target Normal Sheath Acceleration (TNSA) scheme of accelerating particles. The acceleration gradient is 100-1000 GV/cm for 100 to 1000 TeraWatt laser. As the ion-electron double layer is accelerated as a whole by the radiation force or pressure or the laser ponderomotive force, the laser reflectivity $|R|^2$ becomes less than 1, and the radiation force on the double layer per unit area becomes $F=(I_0/c(1+|R|^2)$, where $I_0$ is the intensity of the laser beam. If the velocity of the double layer is $V_f$, the work done by the ponderomotive force per unit area per second is $FV_f$, hence the reflected power per unit area $I_0|R|^2=I_0-FV_f$. This gives:

$$|R|^2 = \frac{1-V_f/c}{1+V_f/c},$$

which gives:

$$F = \frac{2I_0/c}{1+V_f/c}. \tag{13}$$

Further, the intensity of incident radiation on the moving front is reduced by a factor $(1-V_f/c)$ due to the stretching of the pulse (a portion of the pulse in time interval dt impinges on the moving sheath in time $dt'=dt/(1-v_f/c)$), the Doppler effect, so the radiative pressure on a moving over-dense double layer is:

$$F=(2I_0/c)(1-V_f/c)/(1+V_f/c), \tag{14}$$

which is the radiation pressure considered here is the normal incidence on a perfectly reflecting moving mirror. The ions are accelerated by the space-charge electric field induced by the separation of the electrons and ions in plasmas. This leads to an acceleration of the plasma slab as a whole by the radiation pressure.

The mass per unit area of the double layer is $m_i n_0 l_s$ where $m_i$ is the ion rest mass, $n_0$ is the number of ions and the number of electrons, which are assumed to be equal, and $m_i n_0 l_s$ is the mass of the double layer, in a 1D geometry along the z-axis. The total rest mass density is $n_0 m_i$. Solving the equation of motion of the monoenergetic ions of the foil:

$$\frac{d(\gamma_f V_f)}{dt} = \frac{F}{m_i n_0 \Delta_s};$$

which gives:

$$\frac{d(\gamma_f V_f)}{dt} = \frac{2I_0}{m_i n_0 l_s c} \frac{1 - V_f/c}{1 + V_f/c}, \quad (15)$$

where $\gamma_f = (1-V_f^2/c^2)^{-1/2}$ is the relativistic gamma factor, which gives:

$$\left(\frac{1+V_f/c}{1-V_f/c}\right)^{3/2} + 3\left(\frac{1+V_f/c}{1-V_f/c}\right)^{1/2} = 6P\frac{t}{T_L} + 4, \quad (16)$$

where the dimensionless parameter $P=2I_0T_L/(m_ic^2n_0l_s)=4\pi (m/m_i)a_0^2\omega/\omega_p$ and $T_L=2\pi/\omega$ is the temporal laser period. The solution of Equation (15) can be expressed as:

$$V_f/c = \frac{g(t)^2 - 1}{g(t)^2 + 1}, \quad (17)$$

where $$g(t) = \frac{-2 + 2^{1/3}\left(h(t) + \sqrt{4 + h(t)^2}\right)^{2/3}}{2^{2/3}\left(h(t) + \sqrt{4 + h(t)^2}\right)^{1/3}} \text{ and}$$

$$h(t) = 6P\frac{t}{T_L} + 4.$$

Figure 10:
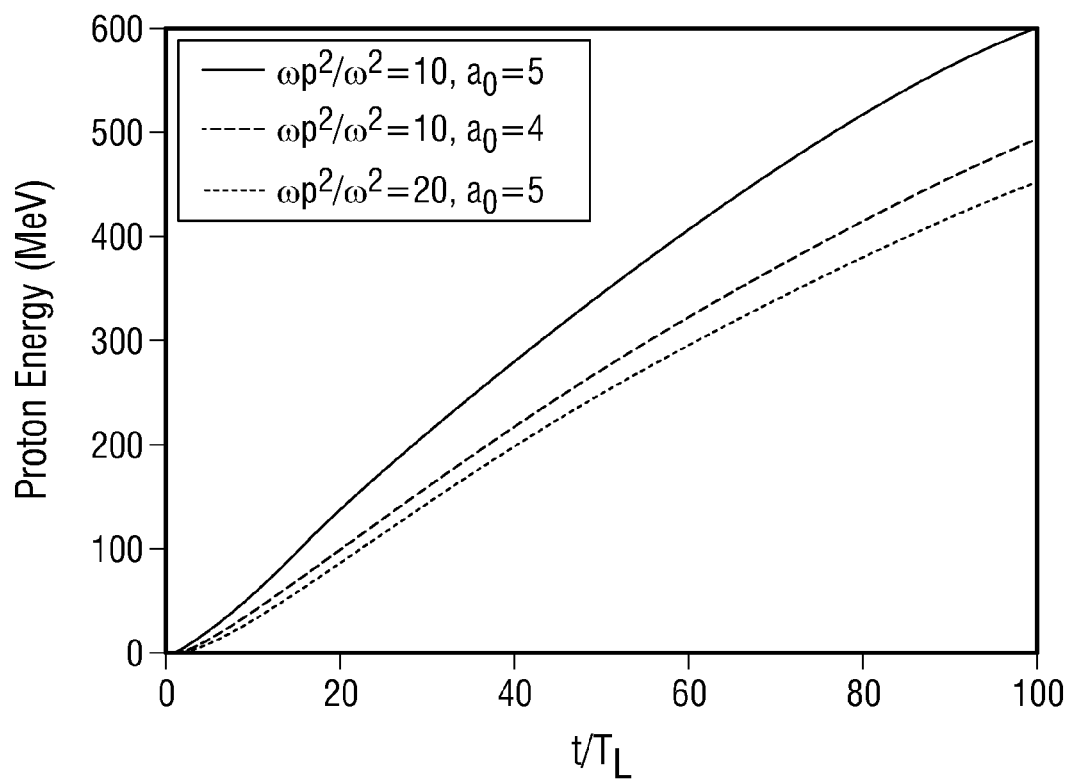
FIG. 10 shows a plot of proton energy produced by the laser proton acceleration system, as a function of time, for a variety of values of $a_0$ and $$\frac{\omega_p^2}{\omega^2};$$

Ion energy can be expressed as:

$$\epsilon_i(t) = (\gamma_f - 1)m_ic^2 = ((1-V_f^2/c^2)^{-1/2} - 1)m_ic^2, \quad (18)$$

with $V_f/c$ given by Equation (16). These are the ions trapped in a self-organized double layer that is formed by the balance of the electrostatic attractive potential of the electrons and the inertial force of the accelerating frame. These trapped ions form a cluster of monenergetic ions in phase space. Controller 112 may select system parameters including laser power and laser pulse duration, in accordance with Equation (18) with $V_f$ obtained from Equation 17 to tune the energy. Equation (18) together with (17) can be used to tune the particle energy by adjusting the laser power and laser pulse duration. But:

In the limit for $t/T_L \ll 1$, $\epsilon_i(t) \propto t$; and for $t/T_L \gg 1$, $\epsilon_i(t) \propto t^{1/3}$. For $m_i/m=1836$, $a_0=5$, $\omega_p^2/\omega^2=10$ $P\cong 0.016$. The time for ion acceleration to 200 MeV is $\sim 30T_L \sim 90$ fs. FIG. 10 shows the variation of ion energy $\epsilon_i$, which here is proton energy, as a function of time for a variety of values of $a_0$ and $$\frac{\omega_p^2}{\omega^2}.$$

The time for acceleration is limited by laser pulse length or the duration for the double layer to maintain its stable over-dense properties. The ion energy varies nearly linearly with time up to $t/T_L \sim 100$ and then varies more slowly as $t^{1/3}$. Typically for a laser with $T_L=3$ fs and intensity of $7.5 \times 10^{19}$ W cm$^{-2}$ in a plasma with ten times critical density the ion energy gain is ~200 MeV in 90 wave periods. The ion plasma period is noted as 60 fs. With higher $a_0$ the energy gain is faster.

The number of monoenergetic ions N accelerated in this process is given by the product of plasma density with the volume $V=\pi r_0^2 l_s$ where $r_0$ is the radius of the focal spot, $l_s$ is the width $\sim c/\omega_p$ of the last layer, $N=\pi r_0^2(c/\omega_p)n_0 \sim n_0^{1/2}$, which can be $10^{11}$ or higher. N is the number of particles (protons in this case) which can be accelerated by the laser to the required energy.

The conditions are now examined for which the plasma slab is accelerated as a whole, pushed by the radiation pressure, since the slab is in fact plasma. The rigidity or stability is due to the formation of a self-arranged accelerated double layer, which traps the ions and electrons. The formation of the electron layer is due to the balance between the laser ponderomotive force pushing the electrons forward and the electrostatic force by the ions behind, pulling the electrons back. For the ion layer, it is the balance between the electrostatic force of the electrons accelerating them and the inertial force of the acceleration holding them back. The effective potential well of the double layer traps the ions and moves them together as a whole system, which is accelerated by the radiation pressure.

Due to the acceleration, there will also be a group of ions that are untrapped and left behind the accelerated layer, making the plasma slab negatively charged. An ion will be untrapped if the acceleration by the space charge electric field is weaker than the mean acceleration of the whole plasma slab. The forces on an ion in the moving frame of the foil accelerated by the laser radiation are considered here. In this frame, there will be an accelerating force by the electrostatic field and a decelerating inertial force. The balance between these two forces determines whether the ions will be trapped or untrapped. Hence, the effective potential as a sum of the electrostatic and inertial potentials is defined as, $\phi'(z,t) = \phi(z,t) + (F_{rad}/eN_0)z$. In a frame moving with the speed $v(t)$ of the foil, the equation of motion for the ion is then given by:

$$m_i \frac{d(\gamma_i v_i)}{dt} = -e\frac{\partial \phi'}{\partial z} = eE - \frac{F_{rad}}{eN_0} \quad (19)$$

where $E = -\partial \phi/\partial z$ is the electric field.

For applications of the ion acceleration, it is interesting to estimate how many of the ions are trapped in the plasma slab and are accelerated to monoenergetic energies, and how many ions are untrapped and spread out in energy. The loss of the ions will stop when the electric field behind the plasma slab is large enough, e.g., due to untrapped ions, so that the acceleration of an ion by this electric field is as large as the mean acceleration of the plasma slab. A thin plasma slab is assumed of initially an equal number of ions and electrons, in a 1D geometry along the z-axis. Then the electric field behind the accelerated layer is obtained from the Poisson equation $\partial E/\partial z = en_i/\epsilon_0$ as:

$$E_{un} = \frac{eN_{un}}{\epsilon_0} \quad (20)$$

where $N_{un} = \int_0^{z_0} n_i dz$ is the integrated (along the z-axis) number of untrapped ions and $z_0$ is the boundary between trapped and untrapped ions. Using $E=E_{un}$ in Equation (19):

$$m_i \frac{d(\gamma_i v_i)}{dt} = \frac{eN_{un}}{\varepsilon_0} - \frac{F_{rad}}{eN_0} \quad (21)$$

If the right-hand side of Equation (21) is larger than zero, then the ion is falling into the potential well and can be considered as trapped, while if it is less than zero, it can be considered as untrapped. The number of trapped ions can be found when $m_i\, d(\gamma_i v_i)/dt=0$, yielding:

$$\frac{N_{un}}{N_0} = \frac{\varepsilon_0}{e^2 N_0^2} F_{rad} \quad (22)$$

The fraction of the number of trapped ions to the total number of ions is:

$$\frac{N_{tr}}{N_0} = 1 - \frac{\varepsilon_0}{e^2 N_0^2} F_{rad} \quad (23)$$

In particular, all ions are untrapped ($N_{un}=N_0$) when:

$$F_{rad} = \frac{e^2 N_0^2}{\varepsilon_0} \quad (24)$$

and for $F_{rad} > e^2 N_0^2/\varepsilon_0$, one would have a complete separation between the electrons and ions. In this case, the electrons will be accelerated in front of the ions by the radiation pressure, while the left-behind ions will experience a Coulomb explosion due to the electrostatic repulsion. This will result in a large spread in ion energies and will decrease the usefulness of these ions in applications where monoenergetic ions are needed. This information provides the upper limit of the achievable monoenergetic particle number given laser parameters, i.e., radiation pressure and target density and thickness from Equation (23).

In general, the monoenergetic energy produced can be tuned by adjusting properties of the laser pulse 17, including the power or intensity, beam width, and time profile, e.g., the rising slope before the laser reaches a main pulse and the duration of the main pulse. The intensity can be adjusted by controlling power pumped to the laser source 01, and the beam width can be adjusted by adjusting a focusing mirror within the laser source 01, and the time profile. The time profile can be selected to be trapezoidal or Gaussian in time.

6. Pre-Pulse and Contrast Ratio

Short pulses generated by high-energy lasers may ride on top of a broad pedestal that carries a non-negligible fraction of energy. The portion of the pedestal that precedes the main peak is called the pre-pulse. The pre-pulse is much less intense and the contrast ratio is a measure of the relative intensity between the main peak and pre-pulse. For this laser acceleration to be efficient, it is also important to minimize the pre-pulse by using a high contrast ratio laser so that the pre-pulse is sufficiently reduced to avoid pre-plasma creation. For a several hundred Tera-Watt laser, a contrast ratio of $10^9 \sim 10^{11}$ or higher is sufficient, wherein better results are achieved with a higher contrast ratio. Otherwise, the pre-pulse may produce a low density plasma corona ahead of the target. The main laser pulse that interacts with the lower density plasma can produce hot electrons by Raman, two-plasma, or other parametric instabilities, reducing the efficiency.

The contrast ratio is controlled by providing the laser source 01 with at least two plasma mirrors that are impacted by the laser pulse 17. The plasma mirrors are configured, e.g., by their shape and position to achieve a desired contrast ratio. It is envisioned that that contrast ratio can be controlled by the controller 112 by selecting plasma mirrors from a variety of plasma mirrors and positioning the plasma mirrors. FIG. 3 in the Reference No. 4, which is incorporated herein by reference, shows an example of the use of plasma mirrors to achieve a desired contrast ratio.

7. R-T Instability Suppression

R-T instability can limit the acceleration achieved by RPA and undesirably broaden the proton beam's energy spectrum so that fewer protons carry the desired energy. For effective acceleration and production of monoenergetic particles, it is important to maintain the target density as overdense (density above the critical density). During the acceleration, R-T instability can develop and form interleaving high density blobs and low density regions. The density difference between high and low density region can grow very rapidly and filaments, or fingerlike structures, can be further developed. Once the density of the low density region of the foil is below critical density, the laser light can penetrate that region, the target will be heated, and particle energy spread will be largely increased. This leads to a leakage of radiation from the target by self-induced transparency, preventing the production or maintenance of monoenergetic particles.

While the accelerating double layer may be stable in one-dimension, it may be unstable in two or three dimensions due to R-T instabilities. However, even in the presence of the R-T instabilities 250-300 MeV energy protons can be achieved while using a laser power of sub-PetaWatt. In selected parameter regimes the nonlinear development seems to smear out the density fingers and maintain the double layer with electrons and ions trapped within. The selected parameters include laser power, laser beam profile such as 501, 502, 503, super Gaussian or wide Gaussian, the thickness and shape of the target 104, target design with sub-wavelength structures, and applying an external axial magnetic guiding field as FIG. 17.

Figure 11:
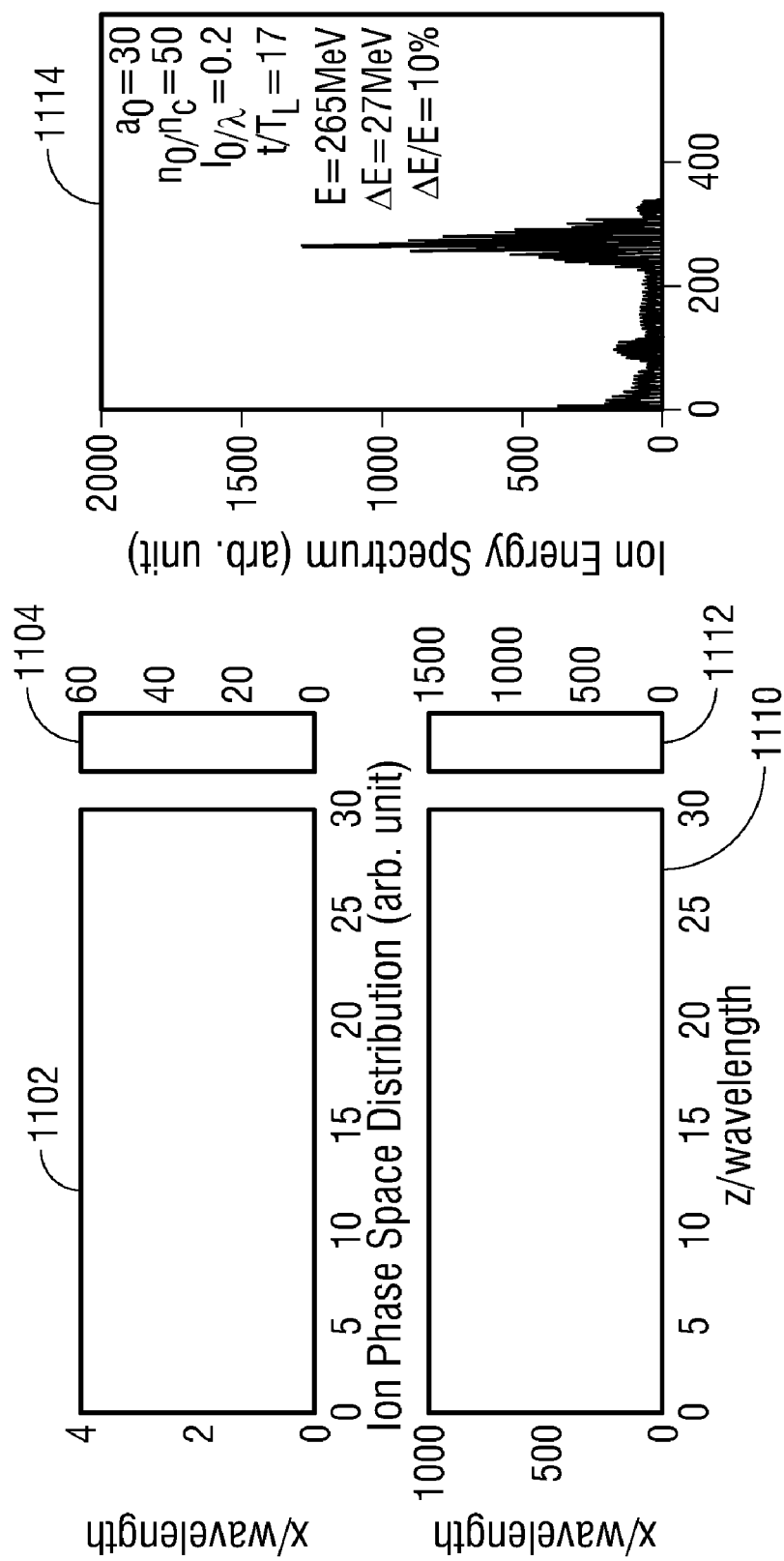
FIG. 11 shows results of two-dimensional particle-in-cell (PIC) simulations of laser-proton target acceleration using the laser proton acceleration system.

FIG. 11 shows results of two-dimensional particle-in-cell (PIC) simulations of laser-proton target acceleration. In FIG. 11, sub-petawatt laser pulses were directed at a target. Frame 1102 shows the proton density distribution. Here proton density is normalized by the critical density. Frame 1104 shows a gray-scale bar for frame 1102 and indicates the value of proton density normalized by the critical density. Frame 1110 shows the phase space distribution of protons in momentum time c (defined as $p_{pz}c=\gamma m_p v_z c$, where $$\gamma = \frac{1}{\sqrt{1 - v^2/c^2}},$$

$m_p$, $v_z$ c are proton mass, velocity along the –z direction and speed of light, respectively) vs. z-space. Frame 1112 shows a gray-scale bar for the phase space density. For all of the above, the z-axis represents wavelengths that range from 0-30. $p_{pz}$ represents momentum in the z-direction).

Frame 1114 shows that the R-T instability is suppressed and monoenergetic protons around 250 MeV are produced in 17 waveperiods, or 56.5 fs after the laser pulse 17 hits the target 104. The vertical axis of frame 1114 is the normalized particle number in the simulation. The particle number with energy 10% of the peak energy is about $10^{10}$. The laser power=890 Terawatt, having normalized laser wave amplitude $a_0=30$, target thickness=0.24 and is optimal, and the normalized target density by critical density $n_0/n_c=50$, target face design is flat, laser beam profile is of flat profile (502 of FIG. 5) with radius ~2.5 um. wavelength.

Figure 13:
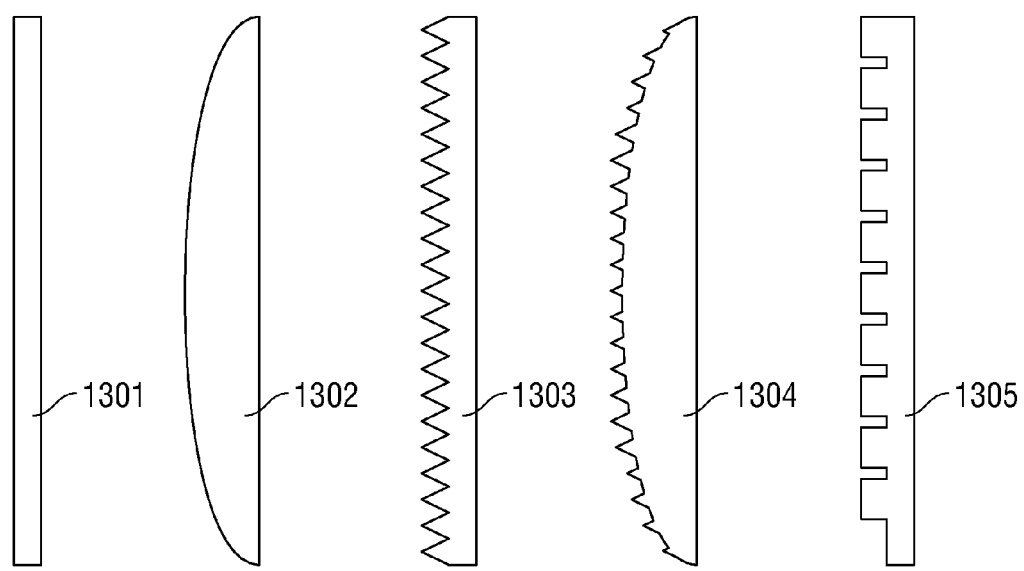
FIG. 13 shows the side view of different embodiments of a target of the laser acceleration system.
Figure 14:
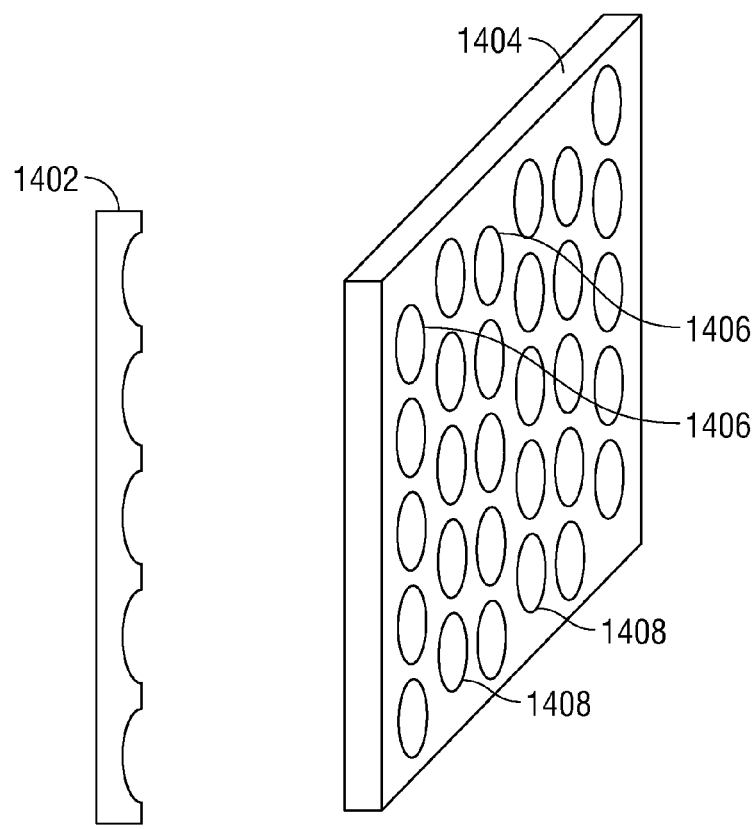
FIG. 14 shows a side view and perspective front view of another embodiment of the target.
Figure 15:
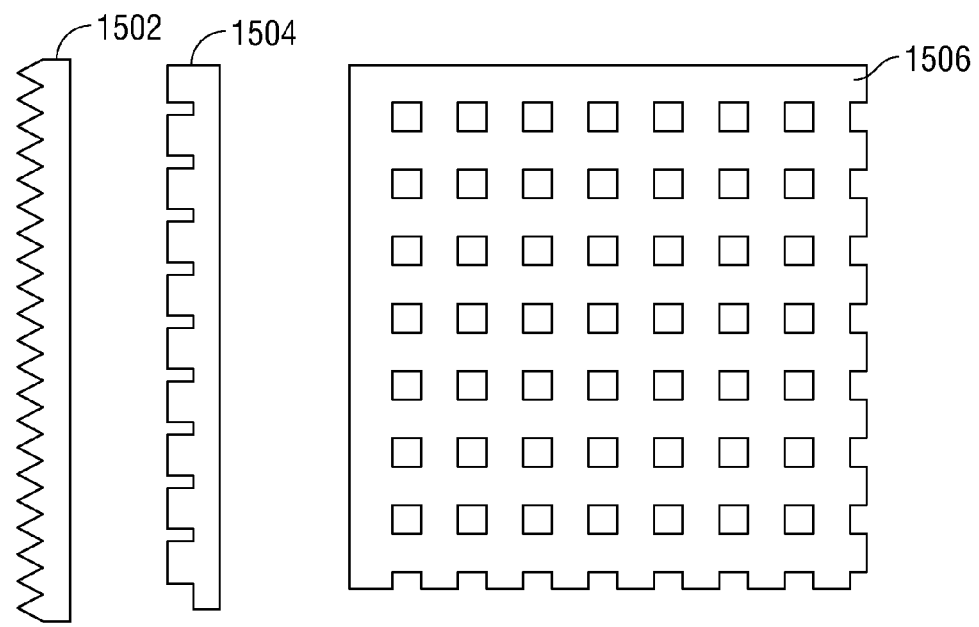
FIG. 15 shows side views and a front view of other embodiments of the target.

FIGS. 13-15 show target designs that suppress R-T instability. FIG. 13 shows the side view of a variety of targets featuring target profiles 1301-1305, all of which are azimuthally symmetric around the z-axis. Target profile 1301 has a uniform thickness, namely the optimal thickness $\Delta_s$. Target profile 1302 has a convex shape. For the convex shape target, the larger number of electron at the center can delay the target from becoming transparent. In the example shown the curvature the curvature is the inverse of the laser beam intensity radial distribution, however this limitation is not required and other curvatures are envisioned.

Target profiles 1303-1305 all have uneven impact surfaces, where the unevenness may be caused by subwavelength protrusions or indentations. The thickest point of each of the profiles 1302-1305 is $<=\Delta_s$. One way to suppress R-T instability is to have subwavelength structures (structures sized to be smaller than the laser wavelength) on the target impact surface to enhance the transverse mixing of electrons and smear out high and low density regions in the transverse direction. This effect will slow down the growth of the low density regions and keep accelerating the target by the laser for a longer time.

Target profile 1303 has uniform pointed saw-teeth protruding from a real or imaginary surface of uniform width. Target profile 1304 has non-uniform pointed saw-teeth protruding from a real or imaginary surface having a curvature. The non-uniformity of the saw-teeth is random, but it is envisioned that it could be in accordance with a pattern. The curvature may be uniform or non-uniform. Target profile 1305 has uniform flat saw-teeth protruding from a real or imaginary surface of uniform width. The periodicity of the teeth (e.g., from rising edge to rising edge or from peak-to-peak) is sub-wavelength, e.g., <the wavelength $\lambda$ of the laser light. A variety of shapes of protrusions or indentations are envisioned, even with different shapes used for the same target profile.

FIGS. 14 and 15 show distribution profiles of indentations and protrusions along the X-Y directions of target impact surface. There are no requirements of symmetry. In FIG. 14 a side view 1402 and perspective view 1404 are provided showing a pattern of concave indentations facing the incident laser along the surface of the target in the X-Y directions perpendicular to the laser propagation direction. The periodicity in both x- and y-direction of the indentations is sub-wavelength. The configuration of indentations may be uniform or non-uniform according to a pattern or randomness.

In the example shown in FIG. 14 there is a series of first one-dimensional arrays 1406 of concave indentations that are spaced along the y-direction, and a series of second one-dimensional arrays 1408 of concave indentations that are also spaced along the y-direction but are displaced in the y-direction relative to the first arrays. The first arrays 1406 are patterned to alternate with the second arrays. Other patterns are envisioned as well. It is envisioned that the indentations shown in views 1402 and 1404 could be formed of any shape and that a combination of different shapes may be used on the surface of one target.

In FIG. 15, side views 1502 and 1504 each show a pattern of protrusions that are spaced along the y-direction. In view 1502 the protrusions are shaped as pointed saw teeth and in view 1504 the protrusions are shaped as flat surfaced saw teeth. Front view 1506 shows a pattern of protrusions configured as a two-dimensional array with the protrusions evenly spaced in the x- and y-directions, with the spacing sub-wavelength in both x- and y-direction. Other patterns are envisioned as well. The protrusions shown in view 1506 may be of any shape, such as the shapes shown in views 1502 or 1504. Other shapes are envisioned as well, including using a combination of shapes on the impact surface of one target. It is also envisioned that a target surface may be provided with a pattern including a combination of protrusions and indentations.

Having subwavelength structure on the target impact surface can enhance the transverse mixing of electrons and smear out the high and low density region in the transverse direction due to the development of R-T instability. Therefore, it will slow down the growth of the low density region and keep accelerating the target 104 by laser for a longer time. In this way, the R-T instability is suppressed.

8. Additional Target Design Features

For medical treatment applications, such as cancer treatment, the target material may be formed of Carbon or $C_2H_4$. The latter has a high molecular density and a high concentration of protons and is compatible with the human body. When the target is formed of a low mass material it is easier to accelerate with RPA. While a pure proton material would be desirable, readily available hydrocarbon targets, such as a diamond-like carbon (DLC) or $C_2H_4$ foil, are acceptable. Carbon ions and protons are considered of complementary value for hadronic cancer therapy, such as by achievement of carbon ion therapy having an energy of ~1-4 GeV and proton therapy having an energy of 70-250 MeV.

Figure 16:
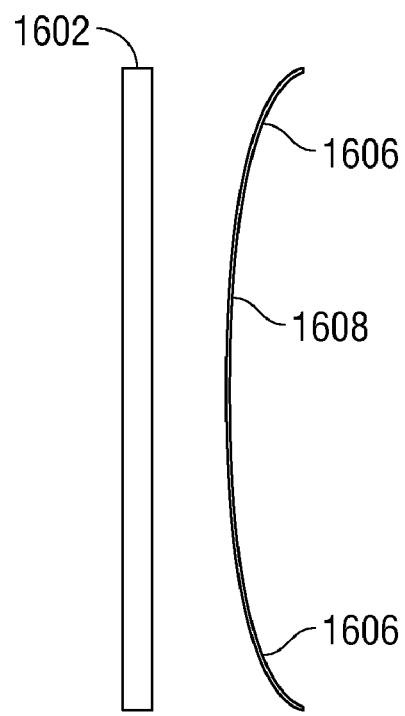
FIG. 16 shows a density profile of a target compared to a side view of the target for another embodiment of the target.

FIG. 16 shows a target design in which the target has a radial density gradient. View 1602 is a side view of a target having a uniform thickness, namely the optimal thickness $\Delta_s$ and a smooth surface along the face lying in the x-y plane. The physical shape of the target it not limited to this design, and could be according to any of the designs described with respect to FIGS. 13-15. View 1604 shows an example of a density profile of the target, where the target has a radial density gradient in which the density of the target varies in relation to the z-axis. The density may vary along the x- and or the y-axes. The density gradient in the radial direction can induce a self-generated magnetic field in the axial direction which can help stabilize the particle beam. A low density is provided at peripheral areas 1606, and a maximum density is provided at central area 1608 of the target. Other density profiles are envisioned.

9. Magnetic Field

FIG. 17 shows the external magnetic guiding field 1702 directed in the z-direction which is generated normal to the target 104. The effect of the magnetic guiding field 1702 is to confine the electrons around the axis along the z-direction. While the laser light pushes the electrons away from the axis, the magnetic guiding field prevents the particles from moving off of the z-axis and stabilizes the double layer. The off axis movement of the electrons, if not prevented, may cause the target 104 to become transparent to the laser radiation pressure.

10. Applications

Proton energy therapy is well suited for cancer treatment, particularly once the systems for providing the therapy become affordable and compact. Proton beams have favorable ballistic and range properties that are attractive for cancer treatment. Proton energy treatment minimizes damage to surrounding tissues near a cancerous growth in a patient's body. For use in proton therapy of cancer, 200 MeV protons can be accelerated within about 100 laser periods using a few Sub-Peta-Watt laser source.

In this design, the accelerator size is greatly reduced due to the high acceleration gradient of the laser pulse 17. The transport path of the laser beam at any combination of its stages including laser beams 02 and 05, laser pulse 17, and particle beams 22, 23, 24, and 25 is also greatly reduced by steering the laser beam 02 and 05 to a selected treatment room 102 to accelerate the target 104 in the selected treatment room 102. In this way the particle beam in all of its stages 22, 23, 24, and 25 is produced locally inside the selected treatment room 102. Therefore, the overall size and cost of the laser delivery system 100 is reduced. It is envisioned that the laser accelerator system 100 for particle therapy treatment use with a configuration having four treatment rooms 102 as in shown in 100 can be less than 40 meter×20 meter. The size of a configuration with a single treatment room 102 can be less than 15 meter×20 meters.

Other applications for proton therapy delivered by a compact laser proton acceleration system 06 include medical radiograph and tomography, production of isotope synthesizer for positron emission tomography (PET) and computer tomography (CT) medical diagnostics, Boron neutron capture therapy (BNCT), high energy physics colliders, production of isotopes for nuclear medical diagnostics and treatment, space electronics radiation testing, hadron therapy, generation of monoenergetic carbon ions for carbon therapy, fast ignition of laser fusion, and high energy physics.

11. Simulation

A series of Vlasov simulations were performed and the results are herein compared with the numerical results deduced from analytical formulae presented above. The simulations demonstrate the 1-dimensional stability of the self-organized double layer, providing a numerical validation of the analytical formulae. Thus verification is provided of the accuracy described above for tuning the energy, selecting system parameters for the laser proton acceleration system 06. The instability suppression is demonstrated with 2D PIC simulation.

The simulations include using a grid-based Vlasov solver to simulate the results of proton acceleration. The grid-based Vlasov solver, unlike a PIC simulation, treats the particle distribution function as a continuous phase fluid that is represented on a grid in both space and velocity (or momentum) space.

The benefit with grid-based Vlasov solvers is that there is no statistical noise in the simulations, and that the dynamical range is determined by the number system of the computer rather than super particles. Hence, the low-density velocity tail of the particle distribution can be resolved much more accurately by grid-based Vlasov solvers.

However, simulations in higher dimensions using grid-based Vlasov solvers are very challenging since the full phase-space has to be represented on a grid, which makes both the storage of the data in the computer's memory, and the numerical calculations, extremely demanding. Also, there is a tendency for the distribution function to become oscillatory in velocity space, which can lead to unphysical noise and recurrence effects in the numerical solution unless proper smoothing or viscosity is used in velocity space. The simulations used here used proper numerical viscosity in configuration space and momentum space to minimize these effects.

The relevant nonlinear kinetic model is now presented, which describes the proton acceleration resulting from the nonlinear interaction between intense laser light and a collisionless plasma. A more detailed derivation of the governing equations is given in Section 12 below. The electromagnetic wave gives rise to the relativistic electron mass increase $m_e \gamma_e$ and a relativistic ponderomotive force, $F_e = -m_e c^2 \partial \gamma_e / \partial z$, where $m_e$ is the electron rest mass, and $\gamma_e = (1 + p_z^2/m_e^2 c^2 + e^2 |A|^2/m_e^2 c^2)^{1/2}$ is the relativistic electron gamma factor and $p_z$ is the z-component of the electron momentum. The relativistic ion mass is $m_i \gamma_i$, and the ponderomotive force acting on the ions reads $F_i = -m_i c^2 \partial \gamma_i / \partial z$, where $m_i$ is the ion rest mass and $\gamma_i = (1 + p_z^2/m_i^2 c^2 + e^2 |A|^2/m_i^2 c^2)^{1/2}$ is the relativistic ion gamma factor. For the ions, the relativistic effects due to the quivering of the ions in the radiation field (proportional to $|A|^2$ inside the ion gamma factor) can usually be neglected due to the large mass of the ions compared to that of the electrons.

The complex envelope of the perpendicular (to the z-axis) vector potential of the circularly or linearly polarized electromagnetic wave is given by the wave equation:

$$\left(\frac{\partial}{\partial t} - i\omega_0\right)^2 A - c^2 \frac{\partial A}{\partial z^2} + \Omega_p^2 A = 0 \tag{25}$$

where:

$$\Omega_p^2 = \frac{e^2}{\varepsilon_0} \int \left(\frac{f_e}{m_e \gamma_e} + \frac{f_i}{m_i \gamma_i}\right) dp_z \tag{26}$$

is the local plasma frequency, accounting for the relativistic mass increase and plasma density variations, and $\omega_0$ is the laser angular frequency. For circularly polarized light, $|A|^2 = |A|^2$, where it is noted that the oscillatory parts of the light cancel exactly. On the other hand, for linear polarization, instead $|A|^2 = |A|^2[1+\cos(2\omega_0 t - 2\phi)]/2$ is the complex phase of A. In this case, $|A|^2$ has an oscillatory part with a frequency twice that of the laser light, which will enter into the ponderomotive force for the electrons. Circularly polarized light is considered below unless stated otherwise. The parallel electric field is obtained from the Maxwell equation:

$$\frac{\partial E_z}{\partial t} = \frac{e}{\varepsilon_0} \int p_z \left(\frac{f_e}{m_e \gamma_e} - \frac{f_i}{m_i \gamma_i}\right) dp_z \tag{27}$$

with initial conditions obtained from Gauss' law:

$$\frac{\partial E_z}{\partial z} = -\frac{\partial^2 \phi}{\partial z^2} = \frac{\rho}{\varepsilon_0} \tag{28}$$

where the electrostatic potential $\phi$ is introduced, and:

$$\rho = e \int (f_i - f_e) dp_z \tag{29}$$

is the electric charge density. The electromagnetic field is coupled nonlinearly with the ions and electrons, whose dynamics is governed by the ion and electron Vlasov equations in the lab frame:

$$\frac{\partial f_i}{\partial t} + \frac{p_z}{m_i \gamma_i} \frac{\partial f_i}{\partial z} + \frac{\partial (-e\phi - m_i c^2 \gamma_i)}{\partial z} \frac{\partial f_i}{\partial p_z} = 0 \tag{30}$$

and $$\frac{\partial f_e}{\partial t} + \frac{p_z}{m_e \gamma_e} \frac{\partial f_e}{\partial z} + \frac{\partial (e\phi - m_e c^2 \gamma_e)}{\partial z} \frac{\partial f_e}{\partial p_z} = 0 \tag{31}$$

respectively. Equations (25), (27), (30) and (31) form a closed set for these purposes.

The simulations below use a box in z-space of size 200 $c/\omega_0$, which was resolved with 2000 grid points. For the electrons, a momentum space was used spanning $\pm 10 m_e c$, resolved with 60 grid points, while the ion momentum space was taken from $-30 m_e c$ to $+1470 m_e c$, resolved with 6000 grid points. An absorbing boundary conditions for the Vlasov equations was used such that the electrons or ions hitting the right or left boundary were absorbed and removed from the simulation. For the electromagnetic wave, an outflow boundary condition was used on the right boundary, the electromagnetic wave of amplitude $A_0$ was injected at the left boundary while absorbing outgoing waves.

The initial conditions for the ions and electrons were taken to be a Maxwellian distribution of the form $f_{i,e}(z,p_z)_{t=0} = \{n_{i,e}(z)/[(2\pi)^{1/2}\alpha_{i,e}]\}\exp[-p_z^2/2\alpha_{i,e}^2]$ with $\alpha_i = 0.8 m_e c$ and $\alpha_e = 0.4 m_e c$, and with the initial ion and electron number density $n_{i,e} = n_0$ in the interval $-L/2 < z < L/2$ and $n_{i,e} = 0$ elsewhere. The computer simulations used a compact Pade scheme to approximate the $p_z$ and x derivatives, while the standard fourth-order Runge-Kutta scheme was used for the time-stepping.

The laser intensity is related to the laser amplitude through:

$$I_0 = \varepsilon_0 \omega_0^2 A_0^2 c = \frac{\varepsilon_0 \omega_0^2 m_e^2 c^3}{e^2} a_0^2 \qquad (32)$$

where $a_0 = e|A_0|/m_e c$ is the normalized amplitude of the injected laser light. A thin plasma slab is assumed with the electron number density $n_0$ and the width L, so that the total number of ions is $N_0 = n_0 L$. In terms of these parameters, the dimensionless parameter P is $$P = \frac{2T_L I_0}{n_0 L m_i c^2} = 2\frac{m_e}{m_i}\frac{\omega_0^2}{\omega_{pe}^2}\frac{\lambda_L}{L}a^2 \qquad (33)$$

where $\omega_{pe} = (n_0 e^2/\epsilon_0 m_e)^{1/2}$ is the plasma frequency of the overdense plasma slab, $\lambda_L = 2\pi c/\omega_0$ is the laser wavelength in vacuum, $\omega_0$ is the laser angular frequency and $m_i/m_e = 1836$ is the proton to electron mass ratio. In terms of the parameters used, the expression for the fraction of the trapped ions (23) can be written as:

$$\frac{N_{tr}}{N_0} = 1 - \frac{2}{(2\pi)^2}\frac{\omega_0^4}{\omega_{pe}^4}\frac{\lambda_L^2}{L^2}\left(\frac{1-v/c}{1+v/c}\right)a^2 \qquad (34)$$

The fraction of the trapped ions is smallest initially when the speed of the foil v is small and increases for larger values of v. Hence, a fraction of the ions initially untrapped may later catch up and again become trapped. In the simulations, plasma slab was used whose density $n_0$ which was 10 times larger than the critical density $n_c = \epsilon_0 m_e^2 \omega_0^2/e^2$ of the laser light, so that $\omega_{pe}^2/\omega_0^2 = 10$, and a laser amplitude of $a = 5$. Three runs were made with different initial thicknesses of the plasma slab, with thickness $L = 0.1\lambda_L$, $L = 0.2\lambda_L$ and $L = 0.4\lambda_L$. In accordance with (34), if:

$$a_0^2 > \frac{(2\pi)^2}{2}\frac{\omega_{pe}^4}{\omega_0^4}\frac{L^2}{\lambda_L^2} \qquad (35)$$

then no ions will be initially trapped and the theory predicts a separation between the electron and ion layers. For $\omega_{pe}^2/\omega_0^2 = 10$, the electron and ion layers will be separated if $a_0 > 4.5$ for $L = 0.1\lambda_L$, $a_0 > 9$ for $L = 0.2\lambda_L$, and $a_0 > 18$ for $L = 0.4\lambda_L$. Hence, for the chosen value $a_0 = 5$, the threshold is exceeded for complete separation of the electron and ion layers for the thinnest slab $L = 0.1\lambda_L$, while the threshold is not exceeded for $L = 0.2\lambda_L$ and $L = 0.4\lambda_L$.

Figure 18:
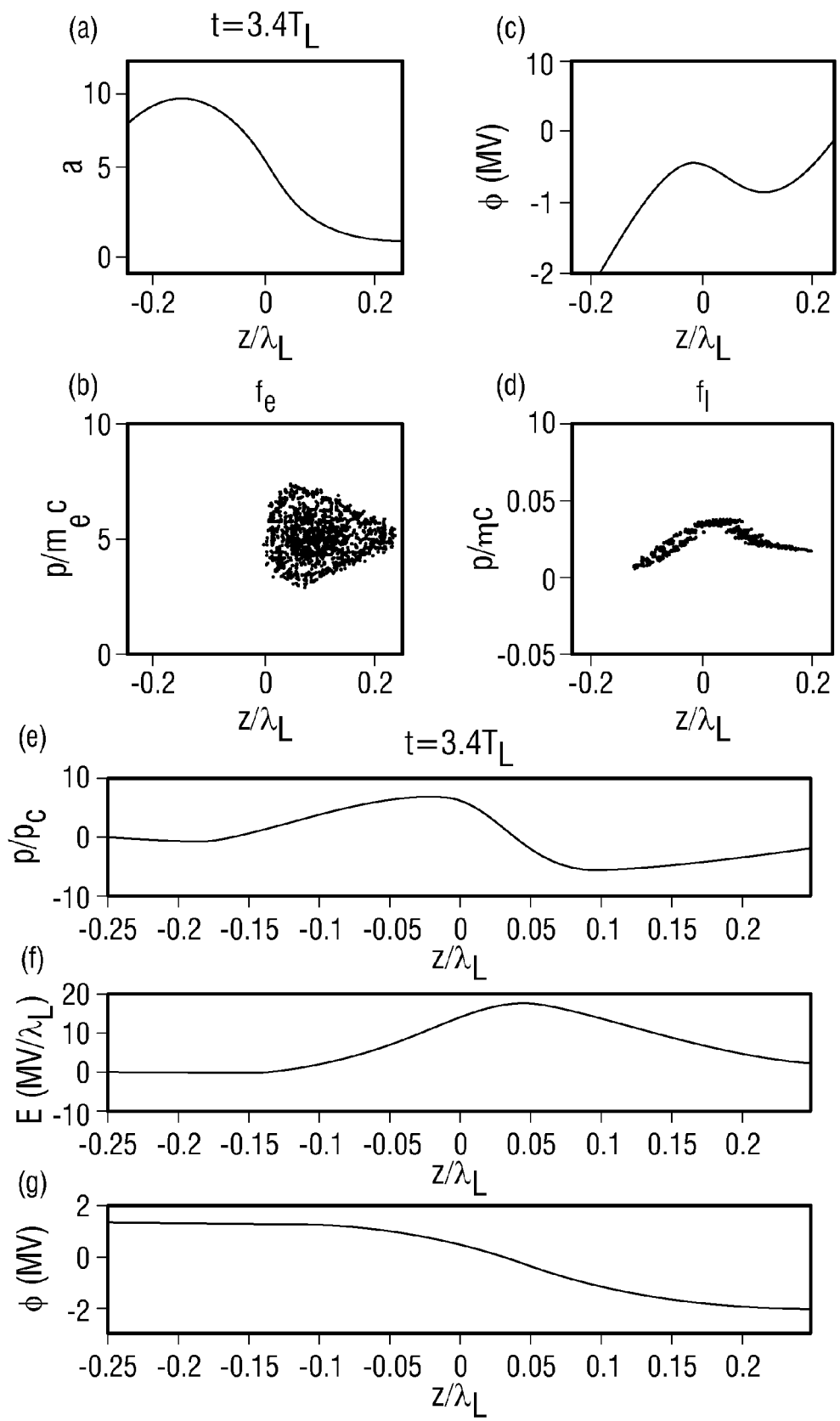
FIGS. 18-25 show a series of plots of results for Vlasov simulations of the laser proton acceleration system.

First the case $L = 0.2\lambda_L$ is discussed. This is close to the optimal thickness $L = (\omega_0^2/\omega_{pe}^2)a_{0,L}/\pi \approx 0.16\lambda_L$ for the monoenergetic ion acceleration. FIGS. 18-21 present details of simulations at different times are. In FIG. 18 simulation results are shown for $t = 3.4 T_L$, for slab thickness $L = 0.2\lambda_L$, where 18(a) shows the laser amplitude, 18(b) shows the electron distribution function, 18(c) shows the effective potential, 18(d) shows the ion distribution function, 18(e) shows the charge density normalized by $\rho_c = en_c$, and 18(f) shows the electric field and (g) the electric potential.

FIG. 18(a) shows that the laser amplitude has set up a standing wave pattern behind the plasma layer, with an amplitude of a 10% of its first maximum, i.e. 2 times that of the injected wave. A small portion of the laser light, with an amplitude of $a \approx 1$, has also tunneled through to the right side of the plasma layer. FIG. 18(b) shows the electron distribution function. The electrons, seen in FIG. 18(b), are pushed forward by the laser light but are kept back by the space charge electric field.

The charge density in FIG. 18(e) shows a bipolar structure where the left-hand side is positively charged and the right-hand side negatively charged, giving rise to the localized positive electric field in FIG. 18(e) and the associate double-layer structure of the potential in FIG. 18(f) the effective trapping potential for the ions given in equation (19), which is derived from the sum of the electrostatic and inertial forces, is depicted in FIG. 18(c). The latter shows a local minimum at $z \approx 0.1\lambda_L$ and a maximum at $z \approx 0$. The ions that are to the left of the potential maximum are starting to lag behind the accelerated plasma layer, and can be considered as untrapped. In FIG. 18(c), a bunch of monoenergetic ions at $z = 0$, which coincide with the left edge of the electron layer in FIG. 18(c). This ion bunch is accelerated uniformly by the space charge electric field.

Figure 19:
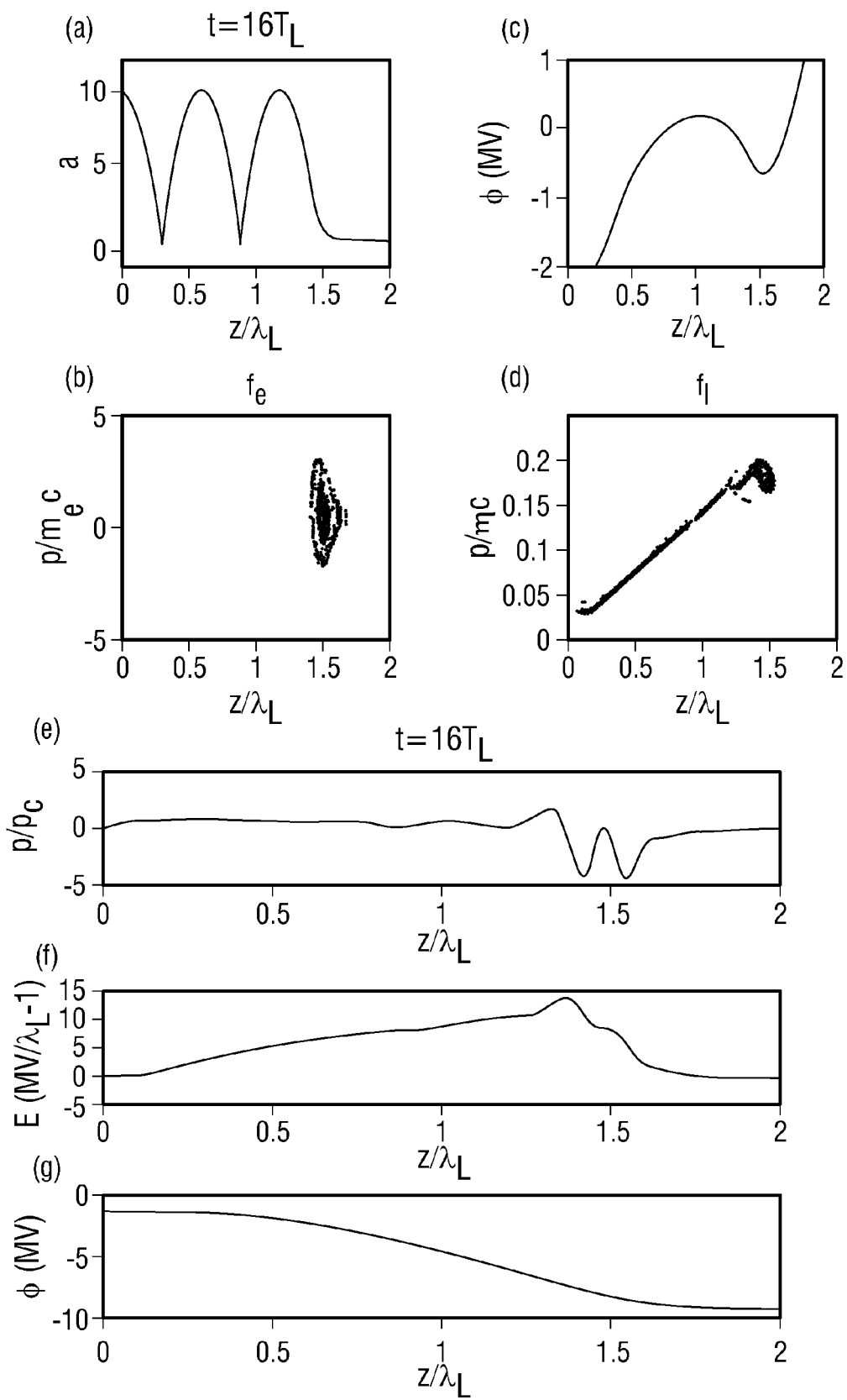

FIG. 19 shows simulation results at $t = 16 T_L$ for slab thickness $L = 0.2\lambda_L$. FIG. 19(a) shows the laser amplitude, FIG. 19(b) shows the electron distribution function, FIG. 19(c) shows the effective potential, FIG. 19(d) shows the ion distribution function, FIG. 19(e) shows the charge density, FIG. 19(f) shows the electric field and FIG. 19(g) shows the electric potential.

The effective potential has deepened and broadened further with a minimum at $z = 1.5\lambda_L$ and the local maximum at $z = 1\lambda_L$, making the trapped ions more deeply trapped. The untrapped population of the ions, clearly seen in FIG. 19(d) between $z = 0$ and $z = 1.5\lambda_L$, form an almost homogeneous positive charge density seen in FIG. 19(e) and associated linearly increasing positive electric field and concave potential profile, seen in FIGS. 19(f) and (g). Note that most of the ions are trapped in the bottom of the effective potential well at $z = 1.5\lambda_L$. They have reached a momentum of $\sim 0.2 m_i c$, corresponding to an energy of $\sim 20$ MeV.

Figure 20:
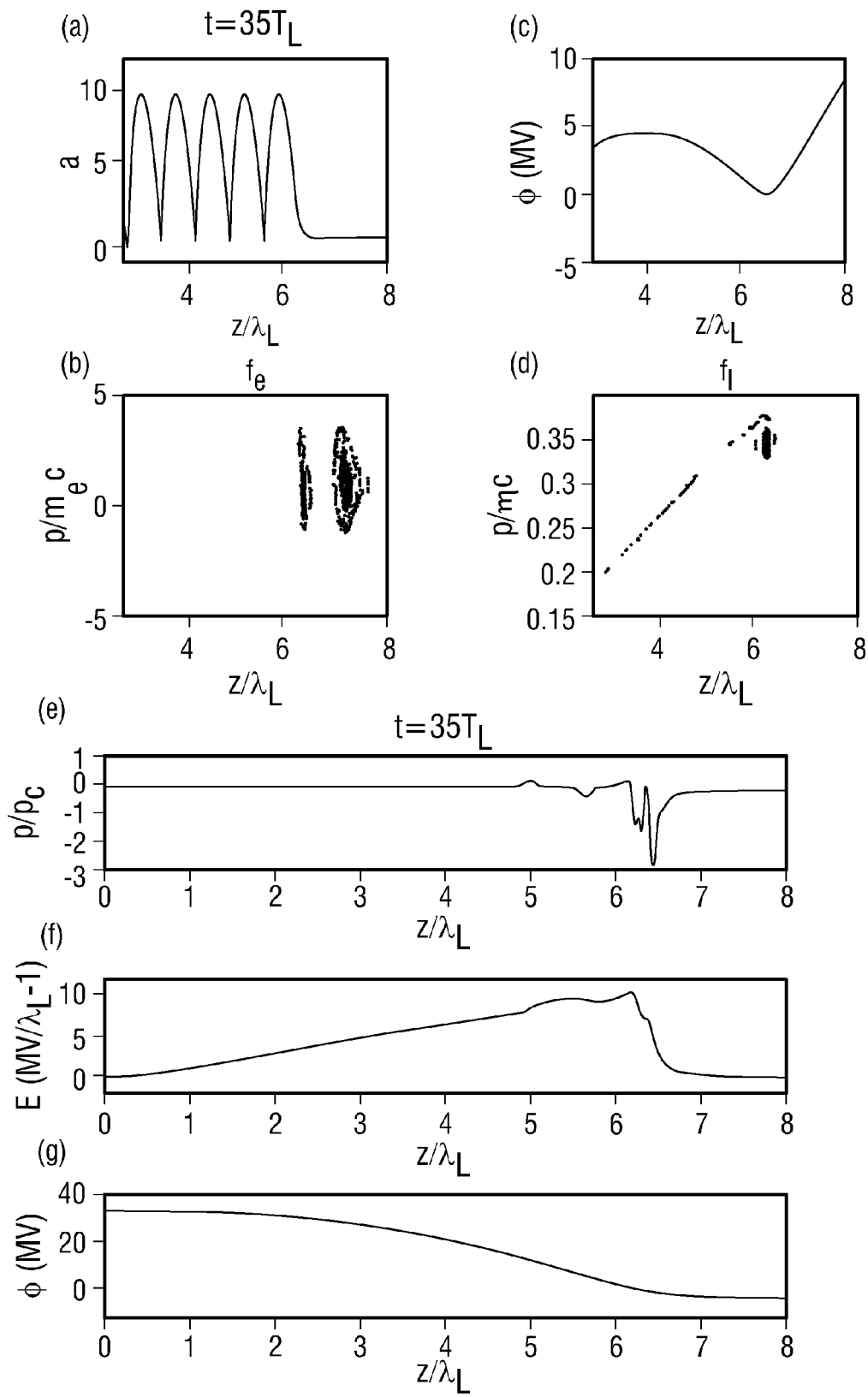

FIG. 20 shows simulation results at $t = 16 T_L$, for slab thickness $L = 0.2\lambda_L$. FIG. 20(a) shows the laser amplitude, FIG. 20(b) shows the electron distribution function, FIG. 20(c) shows the effective potential, FIG. 20(d) shows the ion distribution function, FIG. 20(e) shows the charge density, FIG. 20(f) shows the electric field and FIG. 20(g) shows the electric potential.

The effective potential has deepened and broadened further. Here, the trapped protons have been accelerated to momenta of $0.35 m_i c$ corresponding to a proton energy of ~55 MeV. A portion of the previously untrapped ions begin to fall into the potential and to overtake the trapped ion population at $z \approx 6.5 \lambda_L$. This is due to the decrease of the radiation pressure at higher speeds of the plasma layer by the Doppler shift of the reflected light, giving rise to the factor $(1-v/c)/(1+v/c)$ in the expression for the radiation pressure (13) and in the equation of motion (15). Also here the untrapped population of the ions, seen in FIG. 20(d) gives rise to a linearly increasing positive electric field and concave potential profile, as seen in FIGS. 20 (f) and (g).

Figure 21:
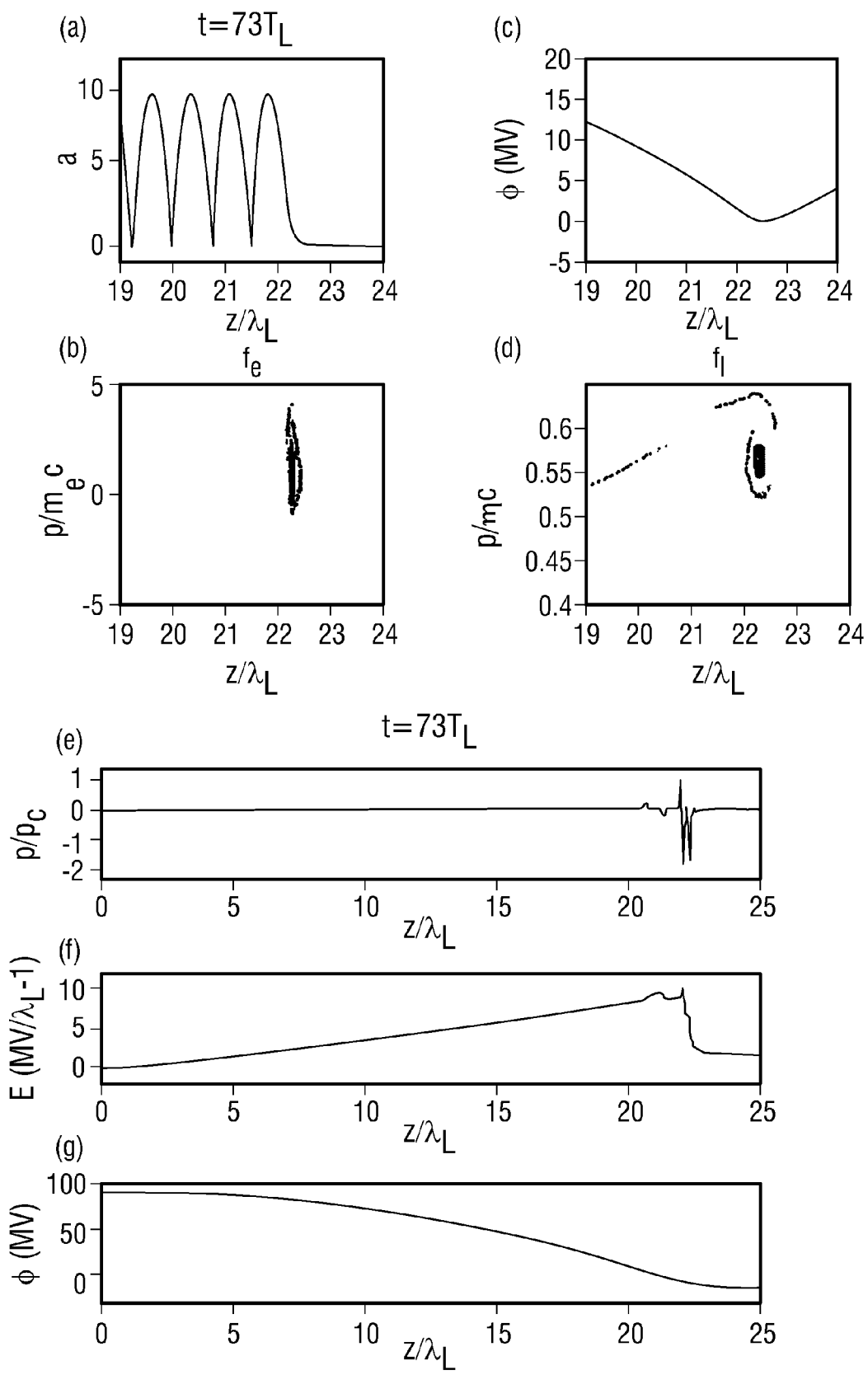

FIG. 21 shows simulation results at $t=73T_L$, for slab thickness $L=0.2\lambda_L$. FIG. 21(a) shows the laser amplitude, FIG. 21(b) shows the electron distribution function, FIG. 21(c) shows the effective potential, FIG. 21(d) shows the ion distribution function, FIG. 21(e) shows the charge density, FIG. 21(f) shows the electric field and FIG. 21(g) shows the electric potential.

FIG. 21 shows that the trapped protons have been accelerated to momenta of $0.55 m_i c$ corresponding to proton energy of ~130 MeV. Previously trapped ions continue to fall into the effective potential minimum and become re-trapped.

Figure 22:
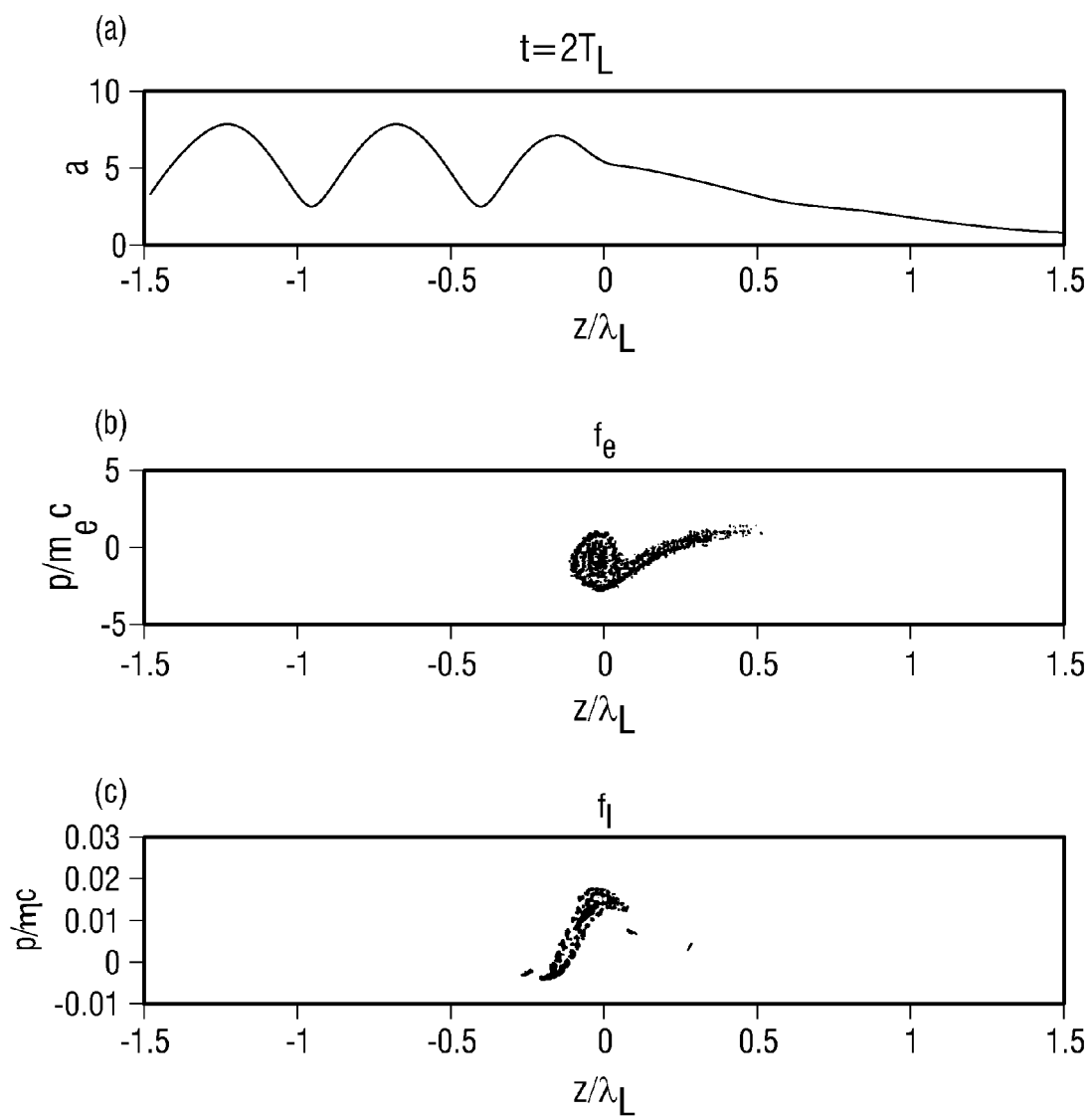

FIG. 22 shows simulation results at $t=2T_L$, for slab thickness $L=0.1\lambda_L$. FIG. 22(a) shows the laser amplitude, FIG. 22(b) shows the electron distribution function and FIG. 22(d) shows the ion distribution function.

FIG. 22 shows the thinnest plasma slab, $L=0.1\lambda_L$. It can be observed that a few laser periods after the laser light has reached the plasma slab, the electrons have not been separated from the ions, but instead the laser light is tunneling through the plasma barrier. The normalized amplitude $a=e|A|/m_e c$ of the laser light is of the order $a \approx 5$ inside the electron slab, so that the relativistic electron mass increase is a factor $\approx 5$, making the plasma less overdense and the thin layer almost completely optically transparent. At this point, the proton acceleration stops and the fastest protons have gained energy of only ~0.2 MeV.

Figure 23:
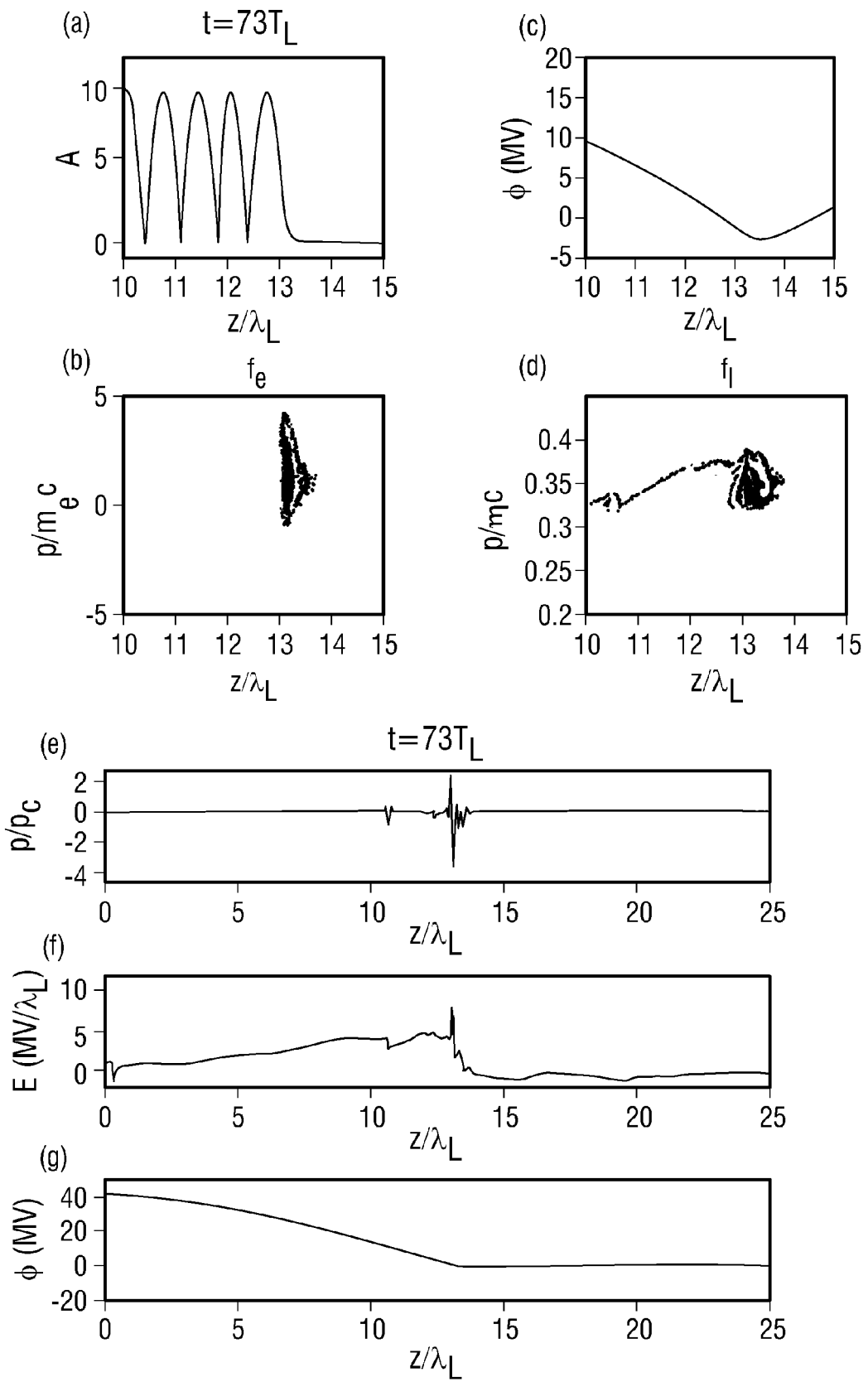

Finally, FIG. 23 shows simulation results at $t=73T_L$, for slab thickness $L=0.4\lambda_L$. FIG. 23(a) shows the laser amplitude, FIG. 23(b) shows the electron distribution function, FIG. 23(c) shows the effective potential, FIG. 23(d) shows the ion distribution function, FIG. 23(e) shows the charge density, FIG. 23(f) shows the electric field and FIG. 23(g) shows the electric potential.

The accelerated ions are less coherent with a larger spread in momentum (and ion energy) than for the thinner foil in FIG. 21. Initially, 'pulsed' acceleration and the production of ion bunches directed towards the plasma slab are observed. The acceleration is slower due to the larger inertial of the thicker slab in FIG. 23. It could be measured that about 95% of the ions are trapped in the effective potential well.

In the RPA discussed here, the laser beam accelerates the whole plasma slab (ions+electrons) as a whole. For this to work, the electron pressure is needed to be sufficiently low so that the plasma slab does not expand by the electron thermal pressure to make the foil transparent, and thus circularly polarized light is preferred since this minimizes the electron heating. Hence, the radiation pressure should be larger than the electron thermal pressure, $2I_0/c > n_0 T_e$.

From the electron distribution function (panel b in FIGS. 18-21 and 23), the electron thermal energy can be estimated to be of the order $T_e \sim 1 m_e c^2$, which should be less than (using the expression (32) for $I_0$), $2I_0/(n_0 c) = 2\epsilon_0 \omega_0^2 m_e^2 c^3 a_0^2/(e^2 n_0 c) = 2 (\omega_0^2/\omega_{pe}^2) a_0^2 m_e c^2 = 5 m_e c^2$, for the parameters used $\omega_0^2/\omega_{pe}^2 = 1/10$ and $a_0 = 5$. Hence, the radiation pressure is here ~5 times larger than the electron thermal pressure and the foil is prevented from undergoing thermal expansion. For the electrons, there is instead a balance between the radiation pressure and the electrostatic force as discussed above. One can compare the theoretical prediction of the energy (18) as a function of time and space to the ones obtained via our Vlasov simulations.

Figure 24:
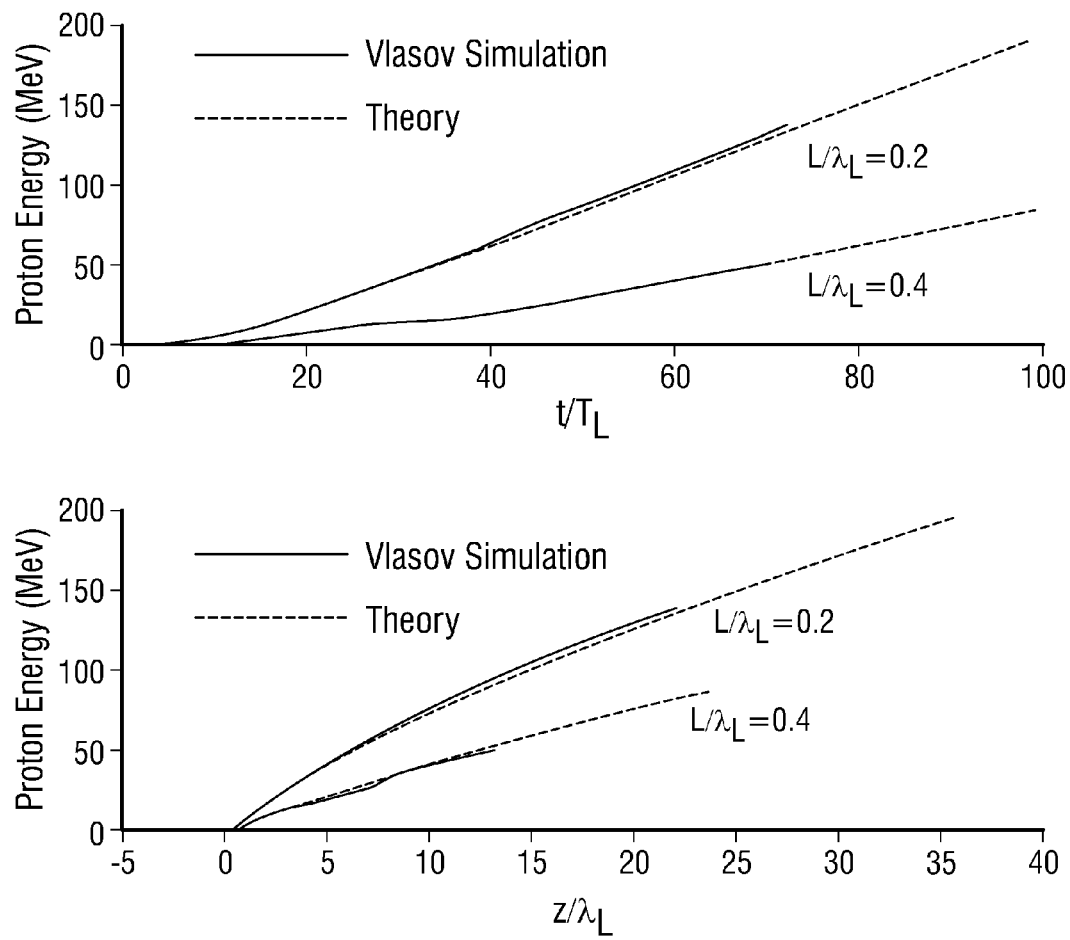

The Vlasov simulation results were obtained by recording the mean position of the trapped ion bunch in phase-space $(z_i, p_i)$, seen in panel (d) in FIGS. 18-21 at each time t and uses that energy of a trapped ion, which is given by $\epsilon_i = m_i c^2 (\sqrt{1+p_i^2/m_i^2 c^2}-1)$. The comparison, displayed in FIG. 24, shows excellent agreement between the theoretical prediction and the numerical results, both for $L=0.2\lambda_L$ and $L=0.4\lambda_L$.

Figure 25:
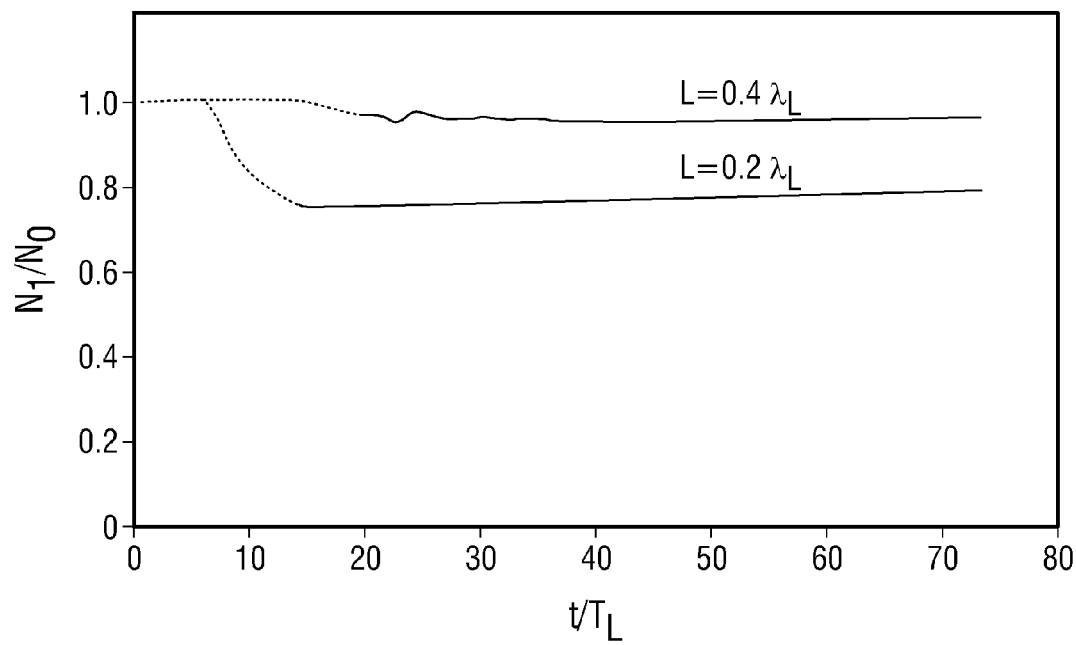

In FIG. 25 the trapped ions are integrated over momentum space and the fraction of the trapped ions obtained in the Vlasov simulations for $L=0.2\lambda_L$ and $L=0.4\lambda_L$ is displayed as a function of time. The dotted lines indicate the initial stage of the acceleration before the trapped and untrapped ions can be distinguished. FIG. 25 shows that about 75-80% of the ions are trapped in the simulation for $L=0.2\lambda_L$, and about 95% are trapped for $L=0.4\lambda_L$. This is approximately what is predicted by equation (34) at small speeds ($v \ll c$). As the accelerated layer increases in speed, the efficiency of the radiation pressure decreases due to the Doppler shift effect. This means that a portion of the untrapped ions starts to overtake the accelerated layer and to be re-trapped as discussed in FIG. 21 and FIG. 23. However, the re-trapping of the untrapped ions is a relatively slow process and there is only a slight increase of the trapped ions in the simulations at later times, where the formula (34) tends to overestimate the number of the trapped ions at later times.

As noted above, simulations in higher dimensions using grid-based Vlasov solvers are very challenging since the full phase-space has to be represented on a grid, which makes both the storage of the data in the computer's memory, and the numerical calculations, extremely demanding. In the study radiation pressure acceleration of protons in multi dimensions, PIC simulation is performed in two dimensions. PIC simulation, such as that used produce the results shown in FIG. 11, has been used to model laser matter interaction for decades. The simulation domain size used is $32\lambda_L \times 24\lambda_L$ divided into $N_x \times N_y = 1024 \times 768$ grids. The foil is made of identical amount of protons and electrons with thickness $L=0.2\lambda_L$ (where $\lambda_L$ is the input laser wavelength) and normalized initial particle density $n_0/n_c=169$, where $n_c = m_e \omega_0^2/(4\pi e^2)$ is the critical density with respect to the input laser frequency. The normalized input amplitude is $a_0=50$. The total amount of computing particles is $10^6$ for each species. Initially, the front surface of the foil is $4\lambda_L$ from the left boundary of the simulation box.

The laser has a Gaussian profile in the transverse direction with the spot size to be $16\lambda_L$ in diameter. The time profile of the laser is a trapezoid shape with $3\lambda_L$ rising, $24\lambda_L$ flat, and $3\lambda_L$ falling in amplitude. Two perpendicularly linear polarized lasers are input with quarter period difference to produce circularly polarization laser beam. The time increment is $(1/180)T_L$, where $T_L$ is the period of the input laser. The energy spectrum of protons is recorded within a window of $2\lambda_L$ width in the center of transverse direction and $0.5\lambda_L$ width in longitudinal direction co-moving with the foil to ensure maximum particle number in the window. It is demonstrated in FIG. 11 that the R-T instability can be suppressed and ~250 MeV monoenergetic protons can be obtained with sub-peta watt laser.

12. Simulation Model

Two simulation models have been used. One is the one-dimension Vlasov simulation and the other one is two dimensional Particle-In-Cell (PIC) simulation.

The derivation of the relevant equations describing nonlinear interactions between intense laser light and a collisionless plasma is now explained for Vlasov simulation. The electromagnetic field is governed by Faraday's and Ampere-Maxwell's equations $$\frac{\partial B}{\partial t} = -\nabla \times E \tag{A.1}$$

and $$\frac{\partial E}{\partial t} = c^2 \nabla \times B - \frac{e}{\varepsilon_0} \int (v_i f_i - v_e f_e) d^3 p \tag{A.2}$$

respectively, where $f_i$ and $f_e$ are the ion and electron distribution functions, and $v_j = p/m_j\gamma_j$ is the velocity of the particle species j (j equals r for the ions and e for the electrons), and $\gamma_j = [1 + (p_x^2 + p_y^2 + p_z^2)/m_j^2 c^2]^{1/2}$ is the relativistic gamma factor, together with the Gauss law $$\nabla \cdot E = \frac{e}{\varepsilon_0} \int (f_i - f_e) d^3 p \tag{A.3}$$

and the divergence condition on the magnetic field $$\nabla \cdot B = 0 \tag{A.4}$$

A 1D geometry is considered along the z-axis. In this geometry, it is convenient to introduce the scalar and vector potentials, $\phi$ and A, respectively, through their relations to the electric and magnetic fields $$E = -\frac{\partial \phi}{\partial z}\hat{z} - \frac{\partial A}{\partial t} \tag{A.5}$$

and $$B = \hat{z} \times \frac{\partial A}{\partial z} \tag{A.6}$$

where A is the vector potential of the electromagnetic wave, which in the Coulomb gauge ($\nabla \cdot A = 0$) is given by $A = \hat{x}A_x + \hat{y}A_y$. Here $\hat{x}$, $\hat{y}$ and $\hat{z}$ are the unit vectors along the x, y and z directions in a Cartesian coordinate system. In accordance with Gauss law:

$$\frac{\partial E_z}{\partial z} = -\frac{\partial^2 \phi}{\partial z^2} = \frac{e}{\varepsilon_0}(n_i - n_e) \tag{A.7}$$

and the parallel (to $\hat{z}$) and perpendicular components of the Ampere-Maxwell laws $$\frac{\partial E_z}{\partial t} = \frac{e}{\varepsilon_0} \int (v_{ez}f_e - v_{iz}f_i) d^3 p \tag{A.8}$$

and $$\frac{\partial^2 A}{\partial t^2} - c^2 \nabla^2 A = \frac{e}{\varepsilon_0} \int v_\perp (f_e - f_i) d^3 p \tag{A.9}$$

respectively.

In a kinetic model for the electrons and ions, Equations (A.5) and (A.6) are used together with the particle momentum equation to obtain:

$$\frac{dp_j}{dt} = q_j(E + v_j \times B) = -q_j\frac{dA}{dt} - q_j\frac{\partial \phi}{\partial z}\hat{z} + \frac{q_j}{\gamma_j m_j} p_j \cdot \frac{\partial A}{\partial z}\hat{z} \tag{A.10}$$

for the particle species j, where the electric charge $q_i = e$ and $q_e = -e$ and the total derivative $d/dt = \partial/\partial t + v_{zj}\partial/\partial z$. Hence, the perpendicular equation of motion is taken to be $p_{j\perp} = -q_j A$, and the parallel equation becomes $$\frac{dp_{zj}}{dt} = -q_j\frac{\partial \phi}{\partial z} - m_j c^2 \frac{\partial \gamma_j}{\partial z} \tag{A.11}$$

where $\gamma_j = (1 + p_{zj}^2/m_j^2 c^2 + e^2|A|^2/m_j^2 c^2)^{1/2}$ is the relativistic ion gamma factor.

The dynamics of the electrons and ions in a collisionless plasma is given by the relativistic Vlasov equation for the electrons and ions. Assuming the plasma to be cold in the JC- and y-directions, the particle distribution functions are $f_i(z, p_x, p_y, p_z, t) = f_i(z, v_z, t)\delta(p_x + eA_x)\delta(p_y + eA_y)$ $f_e(z, p_x, p_y, p_z, t) = f_e(z, v_z, t)\delta(p_x - eA_x)\delta(p_y - eA_y)$, where $\delta$ is the Dirac delta function, and perform the integration in $p_x$ and $p_y$ space. As a result, the dynamics of the electrons and ions parallel to the laser beam is given by the relativistic electron and ion Vlasov equations, respectively, $$\frac{\partial f_e}{\partial t} + \frac{p_z}{m_e \gamma_e}\frac{\partial f_e}{\partial z} + \frac{\partial(e\phi - m_e c^2 \gamma_e)}{\partial z}\frac{\partial f_e}{\partial p_z} = 0 \tag{A.12}$$

and $$\frac{\partial f_i}{\partial t} + \frac{p_z}{m_i \gamma_i}\frac{\partial f_i}{\partial z} + \frac{\partial(-e\phi - m_i c^2 \gamma_i)}{\partial z}\frac{\partial f_i}{\partial p_z} = 0 \tag{A.13}$$

The Maxwell equation for the parallel electric field Equation (A.8) and the electromagnetic wave equation, Equation (A.9) are, respectively, $$\frac{\partial E_z}{\partial t} = \frac{e}{\varepsilon_0} \int p_z \left(\frac{f_e}{m_e \gamma_e} - \frac{f_i}{m_i \gamma_i}\right) dp_z, \tag{A.14}$$

and $$\frac{\partial^2 A}{\partial t^2} - \frac{\partial^2 A}{\partial z^2} + \Omega_{pe}^2 A = 0, \tag{A.15}$$

where $$\Omega_p^2 = \frac{e^2}{\varepsilon_0} \int \left(\frac{f_e}{m_e \gamma_e} - \frac{f_i}{m_i \gamma_i}\right) dp_z \tag{A.16}$$

represents the squared plasma frequency accounting for the electron and ion density variations and relativistic electron mass increase. The ion contribution is typically a factor $m_i/m_e$ smaller than that of the electron contribution, and, in most cases, it can be safely ignored. By using the Ansatz for the circularly polarized electromagnetic wave, viz. $A = (\frac{1}{2}) A(z,t)(\hat{x} + i\hat{y})\exp(-i\omega_0 t) + $ complex conjugate, where $\omega_0$ is the frequency, $|A|^2 = |A|^2$. Equation (A.15) can be written as:

$$\left(\frac{\partial}{\partial t} - i\omega_0\right)^2 A - c^2 \frac{\partial^2 A}{\partial z^2} + \Omega_p^2 A = 0 \quad (A.17)$$

In the limit of linearly polarized light, e.g., A=(½)A(z,t)x̂ exp(−iω₀t)+complex conjugate, Equation (A.17) would still be valid, but then $|A|^2=|A|^2[1+\cos(2\omega_0 t-2\phi)]/2$, where $\phi$ is the complex phase of A. Hence, the ponderomotive force term will in this case have an oscillatory part with a frequency twice that of the laser light, which may lead to chaotic heating of the electrons.

PIC was carried out for two dimensional modeling. Computer simulation of plasma using particle in cell codes is a direct and powerful approach, particularly for investigating kinetic and/or nonlinear effect. There is no need to assign any redundant coefficient. The approach of particle code can be simply described as following: (x,v)→(ρ,J)→(E,B)→(x,v), where x,v,ρ,J,E,B are position, velocity, charge density, current density, electric field, and magnetic field, respectively. From the positions and velocities at any given time, the simulation method includes computing the charge and current densities on a spatial grid sufficiently fine to resolve the collective behavior, and using these charge and current densities to compute the self-consistent electric and magnetic fields via Maxwell's equations. Finally, these fields are used in the equations of motion to advance the positions and velocities of the charged particles. As long as this cycle is executed with a time step sufficiently small to resolve the highest frequency in the problem (which is often the electron plasma frequency,) this approach can be applied to almost all kind of the laser plasma interactions studies.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A proton acceleration system for accelerating protons within a target comprising:
    a laser source generating a laser beam having a wavelength $\lambda_L$ and intensity; and
    a target formed of foil having a selected thickness, wherein the target irradiated by the laser beam and transformed into a plasma having a target density causing a treatment energy to be emitted from the foil due to the irradiation;
    wherein the thickness of the foil of the target is selected so that the foil has a thickness within a range of optimal thickness $\Delta_s$ to $2\times\Delta_s$, wherein $\Delta_s$ is less than the laser wavelength and is a function of the laser intensity, laser wavelength, and target density sufficient to achieve radiation pressure acceleration (RPA).

2. The proton acceleration system according to claim 1, wherein achieving RPA includes balancing a ponderomotive force of the laser radiation accelerating electrons in the foil with a space charge force due to electric field produced by the charge separation pulling the electrons back, wherein protons in the foil are stably trapped due to the balance.

3. The proton acceleration system according to claim 1, wherein $$\Delta_s \cong \frac{4\pi}{\lambda_L}\left(\frac{c}{\omega_p}\right)^2 a_0 = \frac{\lambda_L}{\pi}\left(\frac{\omega}{\omega_p}\right)^2 a_0,$$

wherein:
    $\omega$ is frequency of the laser multiplied by $2\pi$
    $\omega_p$ is the plasma frequency, where plasma frequency is a function of plasma density;
    $\lambda_L$ is the wavelength of the laser;

$$a_0 = \frac{eA_0}{m\omega c}$$

is the normalized electric field amplitude of the wave;
    $A_0$ is the amplitude of linear component of the input laser electromagnetic wave;

$$\vec{E}_i = (\hat{x}+i\hat{y})A_0 e^{-i(\omega t - \omega c/c)},$$

where:
    $\vec{E}_i$ is the electric field of the incident laser;
    $i$ is $e^{i\pi/2}$, a phase difference to produce circular polarization;
    $\hat{x}$ and $\hat{y}$ are the unit vectors along the x and y directions perpendicular to the laser propagation direction z;
    c is the speed of light in vacuum;
    −e is the electric charge of electrons in the foil; and
    m is the mass of the electrons.

4. The proton acceleration system according to claim 1, wherein:
    the laser beam is circularly polarized and has a high intensity with laser power between 100-1000 TeraWatt; and
    the treatment energy includes 50-350 MeV monoenergetic protons.

5. The proton acceleration system according to claim 1, wherein the laser beam includes pre-pulses and a main pulse having a contrast ratio of $>10^9$.

6. The proton acceleration system according to claim 2, wherein the electron layer with the trapped protons is accelerated as whole by laser radiation, achieving an acceleration gradient in the order of >100 GeV/cm.

7. The proton acceleration system according to claim 6, wherein a distance from a reflection mirror of at least one reflection mirror reflecting the laser beam to an area on an object that is treated with the treatment energy is less than three meters.

8. The proton acceleration system according to claim 1, wherein the target density is greater than critical density.

9. The proton acceleration system according to claim 1, wherein the target is formed of $C_2H_4$.

10. The proton acceleration system according to claim 1, wherein the target is shaped to suppress Rayleigh-Taylor (R-T) instability in the target caused by the irradiation.

11. The proton acceleration system according to claim 10, wherein the target is shaped to have a convex front surface that has a maximum thickness substantially at its center and a minimal thickness at its edges.

12. The proton acceleration system according to claim 10, wherein the front surface has a surface level and the shape of the target includes providing the front surface of the target with a plurality of periodic variations in the surface level.

13. The proton acceleration system according to claim 12, wherein the variations in the surface level include at least one of protrusions or indentations.

14. The proton acceleration system according to claim 12, wherein the variations in the surface level are periodical in two-dimensions.

15. The proton acceleration system according to claim 10, wherein the system the target comprises a plurality targets each target having a different combination of thickness and shape, wherein one target is selected from the plurality of targets based on its combination thickness and shape for achieving at least one of maximum RPA and minimal R-T instabilities.

16. The proton acceleration system according to claim 1, wherein the target is provided with a radial density gradient to suppress R-T instability.

17. The proton acceleration system according to claim 1, wherein the treatment energy is tuned by adjusting power of the laser beam that irradiates the target.

18. The proton acceleration system according to claim 1, wherein the laser beam includes pulses and the treatment energy is tuned by controlling duration of the pulses.

19. The proton acceleration system according to claim 1, further comprising a controller having:
   a tangible processor; and
      a memory with instructions to be executed by the tangible processor for tuning the treatment energy by selecting at least one property of the laser beam selected from the group of properties consisting of intensity, time profile, beam width, intensity profile, and contrast ratio.

20. The proton acceleration system according to claim 1, further comprising a controller having:
   a tangible processor; and
      a memory with instructions to be executed by the tangible processor for tuning the treatment energy by selecting the thickness of the target.

21. The proton acceleration system according to claim 1, wherein the laser beam travels along at least one longitudinal path having a transverse profile normal to the at least one longitudinal path;
   the system further comprising at least two mirror shapers impacted by the laser beam before the target is impacted for shaping the intensity distribution of the laser beam's transverse profile.

22. The proton acceleration system according to claim 21, wherein the at least two mirror shapers are shaped so that the intensity distribution is selected from one of double Gaussian, flat top, double super Gaussian, and super Gaussian.

23. The proton acceleration system according to claim 1, wherein the laser beam travels along a longitudinal path;
   the system further comprising a magnet for generating an external magnetic field directed along the longitudinal axis.

24. The proton acceleration system according to claim 1, wherein a particle beam is emitted from the irradiated target, the system further comprising:
   a steering bending magnet for generating a magnetic field that acts on the particle beam; and
   a selector gap for selecting energy of the particle beam that can pass through the selector gap as the treatment energy;
   wherein at least one of energy spread and spot size of the particle beam are determined by a combination of the steering bending magnet and the selector gap.

25. The proton acceleration system according to claim 24, wherein:
   the steering magnet includes at least one coil through which an adjustable current flows for generating the magnetic field; and
   the selector gap includes movable first and second plates that form an adjustable gap between them; and
   the system further comprises a controller having:
      a tangible processor; and
      a memory with instructions to be executed by the tangible processor for controlling at least one of the energy spread and spot size of the particle beam by controlling at least one of:
         the current flowing through the at least one coil; and
         relative positions of the first and second plates for adjusting the size of the gap.

26. A controller for a proton acceleration system including a laser source generating a pulsed laser beam having a wavelength $\lambda_L$ and intensity; and further including a target formed of foil which is irradiated by the laser beam and transformed into a plasma having a target density causing a treatment energy to be emitted from the foil due to the irradiation, wherein the controller comprising:
   a tangible processor; and
   a memory with instructions to be executed by the tangible processor for selecting a thickness of the foil of the target so that the foil has a thickness within a range of optimal thickness $\Delta_s$ to $2 \times \Delta_s$, wherein $\Delta_s$ is less than the laser wavelength and is a function of the laser intensity, laser wavelength, and target density sufficient to achieve radiation pressure acceleration (RPA).

27. The controller according to claim 26, wherein:

$$\Delta_s \cong \frac{4\pi}{\lambda_L}\left(\frac{c}{\omega_p}\right)^2 a_0 = \frac{\lambda_L}{\pi}\left(\frac{\omega}{\omega_p}\right)^2 a_0,$$

wherein:
$\omega$ is frequency of the laser multiplied by $2\pi$
$\omega_p$ is the plasma frequency, where plasma frequency is a function of plasma density;
$\lambda_L$ is the wavelength of the laser;

$$a_0 = \frac{eA_0}{m\omega c}$$

is the normalized electric field amplitude of the wave;
$A_0$ is the amplitude of linear component of the input laser electromagnetic wave;

$$\vec{E}_i = (\hat{x} + i\hat{y})A_0 e^{-i(\omega t - \omega c/c)},$$

where:
$\hat{E}_i$ is the electric field of the incident laser;
i is $e^{i\pi/2}$, a phase difference to produce circular polarization;
$\hat{x}$ and $\hat{y}$ are the unit vectors along the x and y directions perpendicular to the laser propagation direction z;
c is the speed of light in vacuum;
−e is the electric charge of electrons in the foil; and
m is the mass of the electrons.

28. The controller according to claim 26, wherein the system includes a plurality of targets and the selecting the thickness of the foil of the target by the controller includes selecting a target from the plurality of targets for achieving maximum RPA.

29. The controller according to claim 26, wherein the a memory further includes instructions to be executed by the tangible processor for adjusting the treatment energy by adjusting a parameter of the laser beam selected from the group of laser beam parameters consisting of: power, duration of the laser beam's pulses, time profile, beam width, intensity profile, and contrast ratio.

30. The controller according to claim 28, wherein:
the system further comprises a plurality of moveable mirror shapers impacted by the laser beam before the target is impacted for shaping the intensity distribution of the laser beam's transverse profile; and
adjusting the intensity profile includes selecting at least two mirrors from the plurality of mirrors and adjusting positions of the selected at least two mirrors for achieving a desired intensity distributing.

31. The controller according to claim 26, wherein:
the laser is propagated longitudinally and the system further comprises a solenoid through an adjustable current flows for generating an external magnetic field directed along its longitudinal axis for confining electron's of the foil about the longitudinal axis; and
the a memory further includes instructions to be executed by the tangible processor for adjusting the current for controlling the external magnetic field and the confining.

32. The controller according to claim 26, wherein:
the system further includes:
a steering bending magnet having at least one coil through which an adjustable current flows for generating a magnetic field that acts on the particle beam; and
a selector gap having movable first and second plates that form an adjustable gap between them for selecting energy of the particle beam that can pass through the selector gap as the treatment energy;
wherein the a memory further includes instructions to be executed by the tangible processor for controlling at least one of the energy spread and spot size of the particle beam by controlling at least one of:
the current flowing through the at least one coil; and
relative positions of the first and second plates for adjusting the size of the gap.

33. A method for controlling a proton acceleration system including a laser source generating a pulsed laser beam having a wavelength $\lambda_L$ and intensity; and further including a target formed of foil which is irradiated by the laser beam and transformed into a plasma having a target density causing a treatment energy to be emitted from the foil due to the irradiation comprising:
selecting a thickness of the foil of the target so that the foil has a thickness within a range of optimal thickness $\Delta_s$ to $2 \times \Delta_s$, wherein $\Delta_s$ is less than the laser wavelength and is a function of the laser intensity, laser wavelength, and target density sufficient to achieve radiation pressure acceleration (RPA).

34. The method according to claim 33, wherein:

$$\Delta_s \cong \frac{4\pi}{\lambda_L}\left(\frac{c}{\omega_p}\right)^2 a_0 = \frac{\lambda_L}{\pi}\left(\frac{\omega}{\omega_p}\right)^2 a_0,$$

wherein:
$\omega$ is frequency of the laser multiplied by $2\pi$
$\omega_p$ is the plasma frequency, where plasma frequency is a function of plasma density;
$\lambda_L$ is the wavelength of the laser;

$$a_0 = \frac{eA_0}{m\omega c}$$

is the normalized electric field amplitude of the wave;
$A_0$ is the amplitude of linear component of the input laser electromagnetic wave;

$\vec{E}_i = (\hat{x}+i\hat{y})A_0 e^{-i(\omega t - \omega c/c)}$, where:
$\hat{E}_i$ is the electric field of the incident laser;
$i$ is $e^{i\pi/2}$, a phase difference to produce circular polarization;
$\hat{x}$ and $\hat{y}$ are the unit vectors along the x and y directions perpendicular to the laser propagation direction z;
c is the speed of light in vacuum;
−e is the electric charge of electrons in the foil; and
m is the mass of the electrons.

* * * * *